US008858893B2

(12) United States Patent  
Evans et al.

(10) Patent No.: US 8,858,893 B2
(45) Date of Patent: *Oct. 14, 2014

(54) PROCESS FOR THE PREPARATION OF AN ALKYLENE CARBONATE AND AN ALKYLENE GLYCOL

(75) Inventors: Wayne Errol Evans, Richmond, TX (US); Martin Lysle Hess, Fulshear, TX (US); Marek Matusz, Houston, TX (US); Eugene Marie Godfried Andre Van Kruchten, Amsterdam (NL)

(73) Assignee: Shell Oil Company, Houston, TX (US)

( * ) Notice: Subject to any disclaimer, the term of this patent is extended or adjusted under 35 U.S.C. 154(b) by 69 days.

This patent is subject to a terminal disclaimer.

(21) Appl. No.: 13/591,982

(22) Filed: Aug. 22, 2012

(65) Prior Publication Data

US 2012/0315198 A1 Dec. 13, 2012

Related U.S. Application Data

(62) Division of application No. 12/464,972, filed on May 13, 2009, now Pat. No. 8,273,912.

(60) Provisional application No. 61/053,552, filed on May 15, 2008.

(51) Int. Cl.
*B01J 8/00* (2006.01)
*C07C 29/12* (2006.01)
*C07C 29/10* (2006.01)
*C07D 301/10* (2006.01)

(52) U.S. Cl.
CPC ...... *C07D 301/10* (2013.01); *B01D 2255/2092* (2013.01); *C07C 29/12* (2013.01); *B01D 2255/2022* (2013.01); *B01D 2259/40* (2013.01); *Y02C 10/08* (2013.01); *C07C 29/106* (2013.01); *B01D 2255/104* (2013.01); *B01D 2257/2062* (2013.01)
USPC .......................................................... 422/187

(58) Field of Classification Search
USPC .......................................................... 422/187
See application file for complete search history.

(56) References Cited

U.S. PATENT DOCUMENTS

| | | | |
|---|---|---|---|
| 1,153,564 A | 9/1915 | Nichol |
| 1,422,184 A | 7/1922 | Curne, Jr. |
| 1,529,537 A | 3/1925 | Carmen |
| 1,741,559 A | 12/1929 | Dawson |
| 1,851,312 A | 3/1932 | Huff |
| 2,143,371 A | 1/1939 | Francon |
| 2,378,969 A | 6/1945 | Baiely et al. |
| 2,408,010 A | 9/1946 | Wadley et al. |
| 2,432,423 A | 12/1947 | Hunter |
| 2,491,057 A | 12/1949 | Nevison et al. |
| 2,497,296 A | 2/1950 | Chance, Jr. |
| 2,542,520 A | 2/1951 | Hibshman |
| 2,573,341 A | 10/1951 | Kniel |
| 2,588,323 A | 3/1952 | Kniel |
| 2,805,733 A | 9/1957 | Stanton |
| 2,813,920 A | 11/1957 | Cobb, Jr. |
| 2,836,635 A | 5/1958 | Gothel et al. |
| 2,837,587 A | 6/1958 | Hogan et al. |
| 2,942,042 A | 6/1960 | Folz |
| 2,953,608 A | 9/1960 | Fernald |
| 2,973,628 A | 3/1961 | Green et al. |
| 3,000,942 A | 9/1961 | Frankel |
| 3,000,988 A | 9/1961 | Karchmer et al. |
| 3,055,183 A | 9/1962 | Kniel |
| 3,106,462 A | 10/1963 | Cottle |
| 3,169,052 A | 2/1965 | Davison |
| 3,324,194 A | 6/1967 | Kanbayashi et al. |
| 3,326,999 A | 6/1967 | Rhodes, Jr. |
| 3,432,573 A | 3/1969 | Keil |
| 3,456,029 A | 7/1969 | Morita et al. |
| 3,530,199 A | 9/1970 | Lowrance |
| 3,549,719 A | 12/1970 | Duyverman et al. |
| 3,676,516 A | 7/1972 | Haskell et al. |
| 3,844,981 A | 10/1974 | Cusumano |
| 4,059,418 A | 11/1977 | Cull |
| 4,085,192 A | 4/1978 | Van Scoy |
| 4,105,588 A | 8/1978 | Balducci et al. |
| 4,182,722 A | 1/1980 | Lyons |
| 4,729,889 A | 3/1988 | Flytani-Stephanopoulos et al. |
| 4,766,105 A | 8/1988 | Lauritzen |
| 4,822,900 A | 4/1989 | Hayden |
| 4,822,926 A | 4/1989 | Dye |
| 4,831,196 A | 5/1989 | Buonicore et al. |

(Continued)

FOREIGN PATENT DOCUMENTS

| | | |
|---|---|---|
| CA | 2003010 | 1/1991 |
| CN | 1699359 | 11/2005 |
| CN | 1713957 | 12/2005 |
| CN | 1271351 | 8/2006 |
| DE | 2319532 | 10/1973 |

(Continued)

OTHER PUBLICATIONS

PCT International Searching Authority report dated Oct. 28, 2009, for Application No. PCT/US2009/043683 filed May 13, 2009.

(Continued)

*Primary Examiner* — Samantha Shterengarts

(57) ABSTRACT

The invention provides a reaction system for the production of an alkylene carbonate comprising: an epoxidation zone containing an epoxidation catalyst located within an epoxidation reactor; a carboxylation zone containing an bromide-containing carboxylation catalyst located within an alkylene oxide absorber; and one or more purification zones containing a purification absorbent capable of reducing the quantity of bromide-containing impurities in a feed comprising a recycle gas, which purification zones are located upstream from the epoxidation zone; and a process for the production of an alkylene carbonate and an alkylene glycol.

10 Claims, 8 Drawing Sheets

(56) References Cited

U.S. PATENT DOCUMENTS

| | | |
|---|---|---|
| 4,845,296 A | 7/1989 | Ahmed et al. |
| 4,921,681 A | 5/1990 | Ozero et al. |
| 5,145,824 A | 9/1992 | Buffum et al. |
| 5,262,551 A | 11/1993 | Horrell, Jr. et al. |
| 5,322,615 A | 6/1994 | Holtermann et al. |
| 5,334,742 A | 8/1994 | Schon et al. |
| 5,380,697 A | 1/1995 | Matusz et al. |
| 5,466,837 A | 11/1995 | Ramachandran et al. |
| 5,739,075 A | 4/1998 | Matusz |
| 5,756,779 A | 5/1998 | Stavinoha, Jr. |
| 5,801,115 A | 9/1998 | Albers et al. |
| 5,801,259 A | 9/1998 | Kowaleski |
| 5,990,372 A | 11/1999 | Blankenship et al. |
| 6,040,467 A | 3/2000 | Papavassiliou et al. |
| 6,042,798 A | 3/2000 | Masuda et al. |
| 6,080,897 A | 6/2000 | Kawabe |
| 6,124,517 A | 9/2000 | Kaminsky et al. |
| 6,368,998 B1 | 4/2002 | Lockemeyer |
| 6,417,411 B2 | 7/2002 | Kakimoto et al. |
| 6,624,318 B1 | 9/2003 | Muller et al. |
| 6,717,001 B2 | 4/2004 | Evans et al. |
| 6,762,310 B2 | 7/2004 | Neumann et al. |
| 6,939,979 B2 | 9/2005 | Rizkalla et al. |
| 7,132,555 B2 | 11/2006 | Te Raa et al. |
| 2002/0099248 A1 | 7/2002 | Ziaka-Vasileiadou et al. |
| 2003/0017943 A1 | 1/2003 | Shan et al. |
| 2003/0028040 A1 | 2/2003 | Seeba et al. |
| 2003/0098381 A1 | 5/2003 | Mishima et al. |
| 2003/0105376 A1 | 6/2003 | Foral et al. |
| 2004/0175316 A1 | 9/2004 | Bos et al. |
| 2004/0176653 A1 | 9/2004 | Vorberg et al. |
| 2006/0036104 A1 | 2/2006 | Lu et al. |
| 2006/0258529 A1 | 11/2006 | Diefenbacher et al. |
| 2007/0203349 A1 | 8/2007 | Bolk et al. |
| 2008/0182999 A1 | 7/2008 | Rekers et al. |

FOREIGN PATENT DOCUMENTS

| | | |
|---|---|---|
| DE | 2431034 | 1/1975 |
| DE | 2439234 | 2/1975 |
| DE | 2526153 | 1/1976 |
| DE | 2530091 | 1/1976 |
| DE | 2617649 | 11/1977 |
| DE | 3029188 | 4/1982 |
| DE | 3029197 | 4/1982 |
| DE | 3719138 | 12/1988 |
| EP | 003642 | 8/1979 |
| EP | 024628 | 10/1981 |
| EP | 0133763 | 6/1985 |
| EP | 266015 | 5/1988 |
| EP | 288912 | 11/1988 |
| EP | 776890 | 1/2001 |
| EP | 1121977 | 1/2001 |
| EP | 1201301 | 5/2002 |
| EP | 960086 | 10/2002 |
| EP | 1308442 | 5/2003 |
| GB | 580485 | 9/1946 |
| GB | 846077 | 8/1960 |
| GB | 887244 | 1/1962 |
| GB | 1090776 | 8/1964 |
| GB | 1029878 | 10/1964 |
| GB | 1020676 | 1/1965 |
| GB | 2107712 | 5/1983 |
| GB | 2206354 | 1/1989 |
| JP | 59196829 | 11/1984 |
| JP | 2302301 | 12/1990 |
| JP | 5508432 | 11/1993 |
| JP | 2004531542 | 10/2004 |
| JP | 200669591 | 3/2006 |
| JP | 2006512453 | 4/2006 |
| RU | 2228933 | 5/2004 |
| WO | 9200261 | 1/1992 |
| WO | 9709113 | 3/1997 |
| WO | 9722404 | 6/1997 |
| WO | 9736680 | 10/1997 |
| WO | 9829366 | 7/1998 |
| WO | 02053491 | 7/2002 |
| WO | 02088102 | 11/2002 |
| WO | 02094435 | 11/2002 |
| WO | 2004039496 | 5/2004 |
| WO | 2004092148 | 10/2004 |
| WO | 2006045765 | 5/2006 |
| WO | 2008144409 | 11/2008 |

OTHER PUBLICATIONS

Dever, J.P, et al., Ethykene Oxide, Kirk-Othmer Encyclopedia of Chemical Technology, vol. 10, pp. 632-672, Mar. 2004.

Schlauer, Johann, "Absorption, 1 Fundamentals", Wiley-VCH Verlag GmbH & Co. KGaA, pp. 1-3, Oct. 2008.

Rebsdat, Siegfried et al., "Ethylene Oxide", Ulmanns Encyclopedia of Industrial Chemistry, Weinhein, 2005 Wiley-VCH Verlag GmbH & Co., DE, pp. 1-27.

Brunauer, S., et al., "Absorption of Gases in Multimolecular Layers", Bureau of Chemistry & Soils and George Washington University, Feb. 1938, vol. 60, pp. 309-316.

Kirk-Othmer, "Enamels, Porcelain or Vitreous to Ferrites", Encyclopedia of Chemical Technology, 3rd Ed., vol. 9, pp. 445-447.

PROCESS FOR THE PREPARATION OF AN ALKYLENE CARBONATE AND AN ALKYLENE GLYCOL

REFERENCE TO PRIOR APPLICATION

This application is a divisional of U.S. Ser. No. 12/464,972, filed May 13, 2009, which claims the benefit of U.S. Provisional application Ser. No. 61/053,552, filed May 15, 2008, the entire disclosures of which are herein incorporated by reference.

FIELD OF THE INVENTION

The present invention relates to a process for the preparation of an alkylene carbonate and an alkylene glycol from an alkene.

BACKGROUND OF THE INVENTION

Monoethylene glycol is used as a raw material in the manufacture of polyester fibres, polyethylene terephthalate (PET) plastics and resins. It is also incorporated into automobile antifreeze liquids. Ethylene carbonate is typically used as a solvent.

Monoethylene glycol is typically prepared from ethylene oxide, which is in turn prepared from ethylene. Ethylene and oxygen are passed over a silver catalyst, producing a product stream typically comprising ethylene oxide, unreacted ethylene, unreacted oxygen, reaction modifiers, carbon dioxide and water. The amount of ethylene oxide in the product stream is usually between about 0.5 and 10 mole percent. The product stream is supplied to an ethylene oxide absorber and the ethylene oxide is absorbed by a recirculating solvent stream containing mostly water. The ethylene oxide-depleted stream is partially or entirely supplied to a carbon dioxide absorption column wherein the carbon dioxide is at least partially absorbed by a recirculating absorbent stream. Gases that are not absorbed by the recirculating absorbent stream are recombined with any gases bypassing the carbon dioxide absorption column and are recycled to the ethylene oxide reactor.

The solvent stream leaving the ethylene oxide absorber is referred to as fat absorbent. Typically, the fat absorbent is supplied to an ethylene oxide stripper, wherein ethylene oxide is removed from the fat absorbent as a vapour stream. The ethylene oxide-depleted solvent stream exiting the ethylene oxide stripper is referred to as lean absorbent and is recirculated to the ethylene oxide absorber to absorb further ethylene oxide.

The ethylene oxide obtained from the ethylene oxide stripper can be purified for storage and sale or can be further reacted to provide ethylene glycol. In one well-known process, ethylene oxide is reacted with a large excess of water in a non-catalytic process. This reaction typically produces a glycol product stream consisting of almost 90 weight percent monoethylene glycol, the remainder being predominantly diethylene glycol, some triethylene glycol and a small amount of higher homologues. In another well-known process, ethylene oxide is catalytically reacted with carbon dioxide to produce ethylene carbonate. The ethylene carbonate may be subsequently hydrolysed to provide ethylene glycol. Reaction via ethylene carbonate significantly improves the selectivity of ethylene oxide conversion to monoethylene glycol.

The lean absorbent that is supplied to the ethylene oxide absorber is typically aqueous, but in the process disclosed in EP 24 628 the lean absorbent is ethylene carbonate. The fat absorbent, containing ethylene oxide and carbon dioxide dissolved in ethylene carbonate, is sent to a stripper wherein ethylene oxide and carbon dioxide are stripped, and ethylene carbonate is returned as lean absorbent to the ethylene oxide absorber. The stripped ethylene oxide and carbon dioxide are supplied to an ethylene carbonate reactor and react to ethylene carbonate in the presence of an anion-exchange resin, functioning as a carboxylation catalyst.

EP 776 890 discloses a similar process. The lean absorbent that is supplied to the ethylene oxide absorber mainly contains ethylene carbonate and ethylene glycol. The fat absorbent, containing ethylene oxide and carbon dioxide dissolved in ethylene carbonate and ethylene glycol, is supplied directly to an ethylene carbonate reactor wherein ethylene oxide and carbon dioxide react in the presence of a catalyst. The absorption apparatus is operated at low temperature and carboxylation occurs in a subsequent reactor wherein the conditions promote carboxylation.

GB 2 107 712 discloses an alternative process where the gases from an ethylene oxide reactor are supplied directly to a reactor wherein ethylene oxide is converted to ethylene carbonate in the presence of a carboxylation catalyst.

The present inventors have sought to further improve the manufacture of an alkylene carbonate and/or an alkylene glycol from an alkene.

SUMMARY OF THE INVENTION

Accordingly, the present invention provides a reaction system for the production of an alkylene carbonate comprising:
 an epoxidation zone containing an epoxidation catalyst located within an epoxidation reactor;
 a carboxylation zone containing an bromide-containing carboxylation catalyst located within an alkylene oxide absorber; and
 one or more purification zones containing a purification absorbent capable of reducing the quantity of bromide-containing impurities in a feed comprising a recycle gas, which purification zones are located upstream from the epoxidation zone.

The present invention also provides a process for the production of an alkylene carbonate comprising:
 contacting an epoxidation feed comprising an alkene, oxygen, and an epoxidation recycle gas with an epoxidation catalyst in an epoxidation reactor to yield an epoxidation reaction product comprising an alkylene oxide;
 contacting the epoxidation reaction product with a lean absorbent in the presence of a bromide-containing carboxylation catalyst in an alkylene oxide absorber to yield the epoxidation recycle gas and a fat absorbent containing alkylene carbonate; and
 contacting at least a portion of the epoxidation recycle gas with a purification absorbent capable of reducing the quantity of bromide-containing impurities prior to contacting with the epoxidation catalyst.

The present invention also provides a process for the production of an alkylene glycol comprising:
 contacting an epoxidation feed comprising an alkene, oxygen, and an epoxidation recycle gas with an epoxidation catalyst in an epoxidation reactor to yield an epoxidation reaction product comprising an alkylene oxide;
 contacting the epoxidation reaction product with a lean absorbent in the presence of a bromide-containing carboxylation catalyst in an alkylene oxide absorber to yield the epoxidation recycle gas and a fat absorbent containing alkylene carbonate;

contacting the fat absorbent with water in the presence of one or more hydrolysis catalysts to yield a hydrolysis product stream comprising alkylene glycol;

optionally removing water from the hydrolysis product stream in a dehydrator to yield a dehydrated product stream;

optionally purifying the dehydrated product stream to yield a purified alkylene glycol product stream; and contacting at least a portion of the epoxidation recycle gas with a purification absorbent capable of reducing the quantity of bromide-containing impurities prior to contacting with the epoxidation catalyst.

In the process of the invention, the alkylene oxide absorber acts both as an absorber, absorbing alkylene oxide from the epoxidation reaction product, and as a reactor, converting alkylene oxide to alkylene carbonate. Such absorbers are conventionally used for mass transfer processes rather than chemical reactions. In the process of the present invention, carboxylation occurs in the alkylene oxide absorber. Supplying a bromide-containing carboxylation catalyst and lean absorbent at a temperature of at least 60° C. to the alkylene oxide absorber promotes carboxylation in the alkylene oxide absorber, and there is significant conversion of alkylene oxide to alkylene carbonate in the absorber. It has been found that performing the carboxylation reaction in the alkylene oxide absorber using a bromide-containing carboxylation catalyst can result in bromide-containing impurities being introduced into the recycle gas stream. The presence of such bromide-containing impurities in the epoxidation reactor can decrease the performance of the epoxidation catalyst. It has been found that contacting the recycle gas stream with a purification absorbent capable of reducing the quantity of bromide-containing impurities improves the epoxidation process, in particular improves the selectivity, activity, and duration of time the epoxidation catalyst remains in the reactor tubes before having to exchange the catalyst with a fresh epoxidation catalyst.

DETAILED DESCRIPTION OF THE INVENTION

Figure 1:
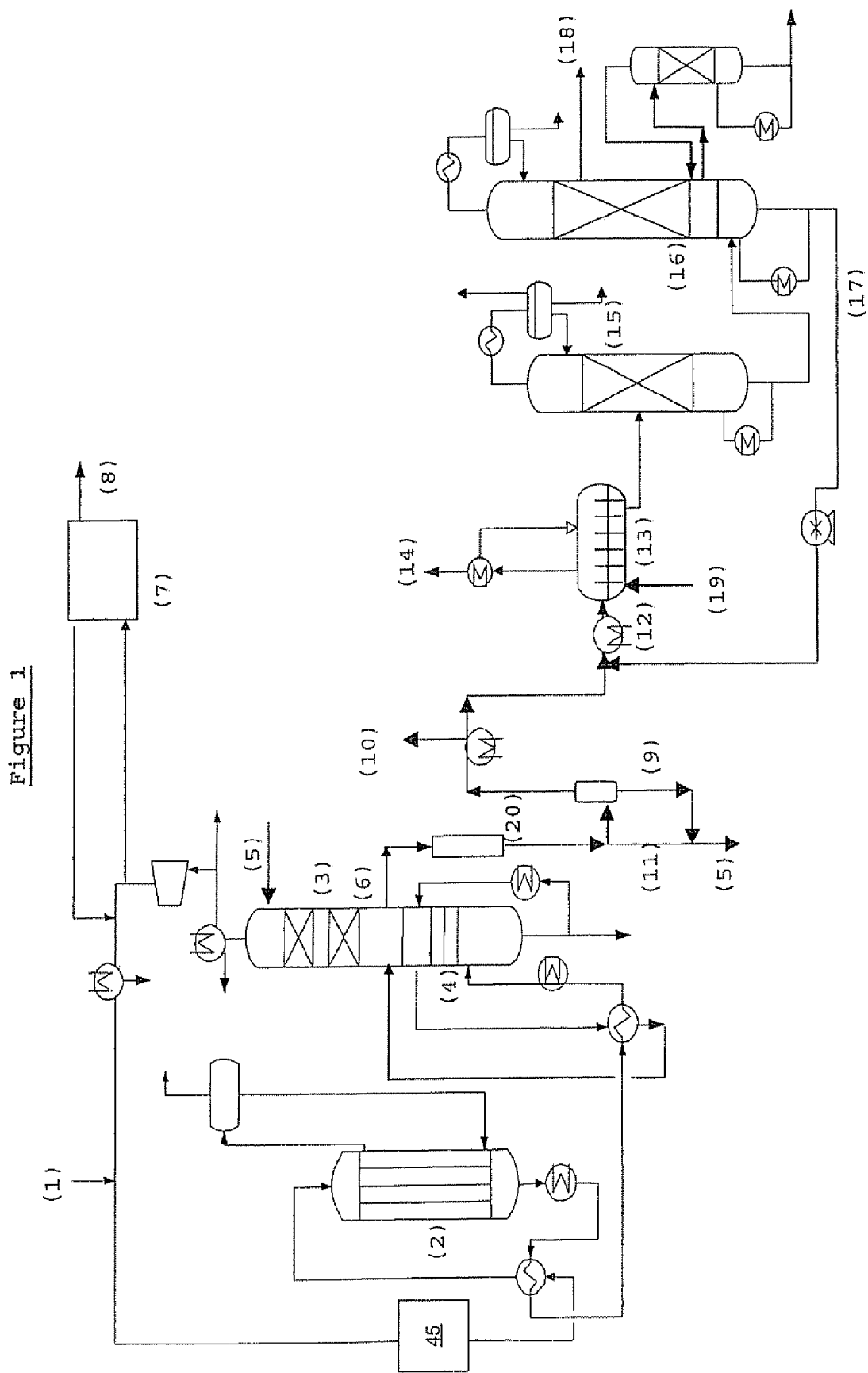
FIG. 1 is a schematic diagram showing a process according to an embodiment of the invention.

The present invention provides a process for the preparation of an alkylene carbonate and/or an alkylene glycol from an alkene:

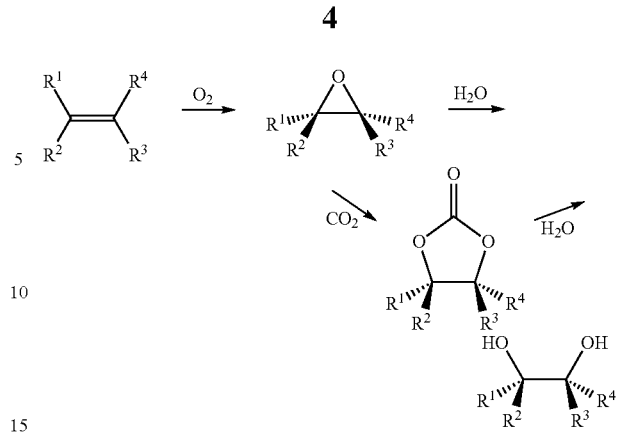

$R^1$, $R^2$, $R^3$ and $R^4$ are preferably chosen from hydrogen or an optionally substituted alkyl group having from 1 to 6 carbon atoms, more preferably from 1 to 3 carbon atoms. As substituents, moieties such as hydroxy groups may be present. Preferably, $R^1$, $R^2$ and $R^3$ represent hydrogen atoms and $R^4$ represents hydrogen or a non-substituted $C_1$-$C_3$-alkyl group and, more preferably, $R^1$, $R^2$, $R^3$ and $R^4$ all represent hydrogen atoms.

Examples of suitable alkenes therefore include ethylene and propylene. In the present invention the most preferred alkene is ethylene.

The epoxidation reactor vessel of the present invention may be any reactor vessel used to react a feed containing alkene and oxygen. The epoxidation reactor vessel may contain one or more open-ended reactor tubes. Preferably, the epoxidation reactor vessel is a shell-and-tube heat exchanger containing a plurality of reactor tubes. The reactor tubes may preferably have an internal diameter in the range of from 15 to 80 mm (millimeters), more preferably from 20 to 75 mm, and most preferably from 25 to 70 mm. The reactor tubes may preferably have a length in the range of from 5 to 20 m (meters), more preferably from 10 to 15 m. The shell-and-tube heat exchanger may contain from 1000 to 20000 reactor tubes, in particular from 2500 to 15000 reactor tubes.

The one or more reactor tubes are positioned substantially parallel to the central longitudinal axis of the reactor vessel and are surrounded by a shell adapted to receive a heat exchange fluid (i.e., the shell side of the shell-and-tube heat exchanger). The heat exchange fluid in the heat exchange chamber may be any fluid suitable for heat transfer, for example water or an organic material suitable for heat exchange. The organic material may be an oil or kerosene. The upper ends of the one or more reactor tubes are connected to a substantially horizontal upper tube plate and are in fluid communication with the one or more inlets to the reactor vessel, and the lower ends of the one or more reactor tubes are connected to a substantially horizontal lower tube plate and are in fluid communication with the one or more outlets to the epoxidation reactor vessel (i.e., the tube side of the shell-and-tube heat exchanger). The epoxidation reactor vessel contains an epoxidation zone comprising a packed bed of catalyst particles. The catalyst bed is positioned inside the one or more reactor tubes.

The purification of the feed components, in particular the recycle gas, occurs within one or more purification zones located outside of the epoxidation reactor vessel and/or within a purification zone positioned inside of the epoxidation reactor vessel.

The terms "substantially vertical" and "substantially horizontal", as used herein, are understood to include minor deviations from true vertical or horizontal positions relative to the central longitudinal axis of the reactor vessel, in particular the terms are meant to include variations ranging from 0 to 20 degrees from true vertical or horizontal positions. True vertical is aligned along the central longitudinal axis of the reactor vessel. True horizontal is aligned perpendicular to the central longitudinal axis of the reactor vessel.

The term "substantially parallel", as used herein, is understood to include minor deviations from a true parallel position relative to the central longitudinal axis of the reactor vessel, in particular the term is meant to include variations ranging from 0 to 20 degrees from a true parallel position relative to the central longitudinal axis of the reactor vessel.

As used herein, the purification absorbent temperature is deemed to be the weight average temperature of the purification absorbent particles in the packed bed.

As used herein, the epoxidation catalyst temperature is deemed to be the weight average temperature of the epoxidation catalyst particles in the packed bed.

In an embodiment, one or more purification zones are located outside of the epoxidation reactor vessel (i.e., separate from the epoxidation reactor vessel). The recycle gas is fed to one or more purification zones before contacting the epoxidation catalyst. One or more additional feed components may also be contacted with the purification absorbent in a purification zone either in conjunction with or separate from the recycle gas. A purification zone may comprise one or more separate purification vessels each containing a packed bed of the purification absorbent.

In this embodiment, the one or more purification zones are located upstream from the epoxidation reactor vessel. Preferably, at least one purification zone is located in the recycle gas loop. The recycle gas loop comprises interconnecting pipework between the alkylene oxide absorber and the epoxidation reactor vessel and optionally includes a carbon dioxide absorber, heat exchangers, compressors, and water removal "knock-out" vessels in the recycle gas loop. Suitably, one or more purification zones may be located anywhere in the recycle gas loop, for example in the recycle gas loop downstream from the addition of the feed components (e.g., ethylene, oxygen, methane and reaction modifier) and upstream from the product/feed heat exchanger which exchanges the heat from the epoxidation reaction product with the feed components to the epoxidation reactor; in the recycle gas loop between the product/feed heat exchanger and the inlet to the epoxidation reactor; in the recycle gas loop upstream from any "knock-out" vessels used to remove water from the recycle gas; in the recycle gas loop between the alkylene oxide absorber and the carbon dioxide absorber, in particular in the recycle gas loop between the alkylene oxide absorber and a compressor positioned in the recycle gas loop prior to the carbon dioxide absorber.

In this embodiment, the packed bed of the purification absorbent in the purification vessel may have any bed height. A purification zone may comprise two or more separate purification vessels. The two or more purification vessels may be arranged in parallel with associated switching means to allow the process to be switched between purification vessels, thus maintaining a continuous operation of the process. Suitable switching means that can be used in this embodiment are known to the skilled person.

In this embodiment, suitably the temperature of the purification absorbent may be at least 25° C., in particular at least 60° C., more in particular at least 70° C. The temperature of the purification absorbent may be at most 325° C., in particular at most 210° C., more in particular at most 200° C., most in particular at most 180° C. In this embodiment, the temperature of the purification absorbent may be in the range of from 25 to 325° C., preferably from 60 to 200° C., most preferably from 70 to 180° C.

In an embodiment, the epoxidation reactor vessel may contain a purification zone comprising a packed bed of purification absorbent positioned upstream from the one or more reactor tubes, for example positioned on top of the/thereof. Preferably, the support material may be alumina, in particular alpha-alumina or gamma-alumina.

In this embodiment, the purification absorbent may be prepared by conventional processes for the production of such metal-containing materials, for example by precipitation or impregnation, preferably by precipitation. For example, in the precipitation process, a suitable salt of copper, optional additional metal salt, and optional salt of the support material may be prepared by reacting the metals with a strong acid such as nitric acid or sulfuric acid. The resulting salts may then be contacted with a basic bicarbonate or carbonate solution in a pH range of from 6 to 9 at a temperature from 15 to 90° C., in particular 80° C., to produce a precipitate of metal oxide. The precipitate may be filtered and then washed at a temperature in the range of from 20 to 50° C. The precipitate may then be dried at a temperature in the range of from 100 to 160° C., in particular 120 to 150° C. After drying, the precipitate may then be calcined at a temperature in the range of from 170 to 600° C., in particular from 350 to 550° C. The precipitate may be formed into a desired size and shape by conventional processes such as extrusion or tableting. Alternatively, an impregnation process may be used to form the purification absorbent by impregnating the support material with suitable solutions of the metal compounds followed by drying and calcining.

In this embodiment, the purification absorbent after calcination may contain metal oxide in a quantity in the range of from 20 to 100% w (percent by weight), relative to the weight of the purification absorbent, in particular from 70 to 100% w, relative to the weight of the purification absorbent, more in particular from 75 to 95% w, relative to the weight of the purification absorbent.

In this embodiment, the support material may be present in the purification absorbent after calcination in a quantity of at least 1% w, relative to the weight of the purification absorbent, in particular at least 1.5% w, more in particular at least 2% w, relative to the weight of the purification absorbent. The support material may be present in the purification absorbent after calcination in a quantity of at most 80% w, relative to the weight of the purification absorbent, in particular at most 50% w, more in particular at most 30% w, relative to the weight of the purification absorbent, most in particular at most 25% w, relative to the weight of the purification absorbent. The support material may be present in the purification absorbent after calcination in a quantity in the range of from 5 to 25% w, in particular from 10 to 20% w, relative to the weight of the purification absorbent.

In this embodiment, when the purification absorbent comprises copper, the purification absorbent after calcination may contain copper oxide in a quantity of at least 1 w (percent by weight), relative to the weight of the purification absorbent, in particular at least 5% w, more in particular at least 8% w, relative to the weight of the purification absorbent. The purification absorbent after calcination may contain copper oxide in a quantity of at most 100% w, relative to the weight of the purification absorbent, in particular at most 75% w, more in particular at most 60% w, relative to the weight of the purification absorbent. The purification absorbent after calcination may contain copper oxide in a quantity in the range of from 8 to 75% w, relative to the weight of the purification absorbent, in particular from 15 to 60% w, more in particular from 20 to 50% w, most in particular from 30 to 40% w, relative to the weight of the purification absorbent.

In this embodiment, when the purification absorbent comprises copper, the purification absorbent after calcination may contain the additional metal oxide and copper oxide in a mass ratio of metal oxide to copper oxide of at least 0.2, in particular at least 0.5, more in particular at least 0.7. The mass ratio of metal oxide to copper oxide may be at most 10, in particular at most 8, more in particular at most 5. The mass ratio of metal oxide to copper oxide may be in the range of from 0.5 to 10, in particular from 1 to 5, more in particular from 1.2 to 2.5, most in particular from 1.25 to 1.75.

In this embodiment, after calcination, the purification absorbent may or may not be subjected to hydrogen reduction. Typically, hydrogen reduction may be conducted by contacting the purification absorbent with a hydrogen reduction stream at a temperature in the range of from 150 to 350° C. A suitable hydrogen reduction stream may contain hydrogen in the range of from 0.1 to 10% v (percent by volume) and nitrogen in the range of from 99.9 to 90% v, relative to the total reduction stream. After hydrogen reduction, the purification absorbent may be subjected to oxygen stabilization. Oxygen stabilization may be conducted by contacting the reduced purification absorbent at a temperature in the range of 60 to 80° C. with a gas stream containing oxygen in the range of from 0.1 to 10% v and nitrogen in the range of from 99.9 to 90% v, relative to the total stabilization stream.

In this embodiment, the purification absorbent may contain a total amount of the metals (measured as the weight of the metal elements relative to the weight of the purification absorbent (e.g., the total weight of the metal elements from the reduced or oxide forms present in the purification absorbent, relative to the total weight of the purification absorbent)) in a quantity in the range of from 15 to 90% w (percent by weight), in particular from 20 to 85% w, more in particular from 25 to 75% w, measured as the weight of the metal elements relative to the weight of the purification absorbent.

In this embodiment, the support material may be present in the purification absorbent in a quantity of at least 1% w, relative to the weight of the purification absorbent, in particular at least 1.5% w, more in particular at least 2% w, relative to the weight of the purification absorbent. The support material may be present in the purification absorbent in a quantity of at most 80% w, relative to the weight of the purification absorbent, in particular at most 50% w, more in particular at most 30% w, relative to the weight of the purification absorbent, most in particular at most 25% w, relative to the weight of the purification absorbent. The support material may be present in the purification absorbent in a quantity in the range of from 5 to 25% w, in particular from 10 to 20% w, relative to the weight of the purification absorbent.

In this embodiment, when the purification absorbent comprises copper, the purification absorbent may contain copper in a quantity of at least 1% w (percent by weight), measured as the weight of the copper element relative to the weight of the purification absorbent (e.g., the weight of the copper element from the reduced or oxide forms present in the purification absorbent, relative to the total weight of the purification absorbent), in particular at least 5% w, more in particular more than 8% w, most in particular at least 20% w, measured as the weight of the copper element relative to the weight of the purification absorbent. The purification absorbent may contain copper in a quantity of at most 85% w, in particular at most 75% w, more in particular at most 60% w, measured as the weight of the copper element relative to the weight of the purification absorbent. The purification absorbent may contain copper in a quantity in the range of from 10 to 75% w, in particular from 15 to 60% w, more in particular from 20 to 50% w, most in particular from 25 to 40% w, measured as the weight of the copper element relative to the weight of the purification absorbent.

In this embodiment, when the purification absorbent comprises copper, the purification absorbent may contain the additional metal(s) and copper in a ratio of the mass of the additional metal(s) present in the purification absorbent to the mass of copper present in the purification absorbent of at least 0.2, in particular at least 0.5, more in particular at least 0.7 (basis the respective elements). The mass ratio of the additional metal(s) to copper may be at most 10, in particular at most 8, more in particular at most 5, same basis. The mass ratio of the additional metal(s) to copper may be in the range of from 0.5 to 10, in particular from 1 to 5, more in particular from 1.2 to 2.5, most in particular from 1.25 to 1.75, same basis.

In a separate embodiment, the purification absorbent may comprise silver, an alkali or alkaline earth metal component, and a support material. When using purification absorbents which contain silver, higher temperatures are preferably avoided when ethylene and oxygen are present in the feed to be treated.

In this embodiment, the purification absorbent may be prepared by co-mulling the components of the purification absorbent. For further description of such co-mulling methods, reference may be made to US 2006/0036104, which is hereby incorporated by reference. Preferably, the silver and the alkali or alkaline earth metal components are deposited on the support material through an impregnation method. For further description of such impregnation methods, reference may be made to U.S. Pat. No. 5,380,697, U.S. Pat. No. 5,739,075, EP-A-266015, and U.S. Pat. No. 6,368,998, which methods are incorporated herein by reference. Methods of depositing silver on a support material include impregnating the support with a silver compound containing cationic silver or complexed silver and performing a reduction to form metallic silver particles. Suitably, silver dispersions, for example silver sols, may be used to deposit silver on the support material.

In this embodiment, the purification absorbent may contain silver in a quantity of at least 5 g/kg, in preferably at least 100 g/kg, more preferably at least 150 g/kg, most preferably at least 200 g/kg, relative to the weight of the purification absorbent. Preferably, the purification absorbent comprises silver in a quantity of from 5 to 500 g/kg, more preferably from 150 to 400 g/kg, for example 105 g/kg, or 120 g/kg, or 190 g/kg, or 250 g/kg, or 350 g/kg, on the same basis.

In this embodiment, the support material may be selected from alumina, titania, zirconia, silica, activated carbon or mixtures thereof. Preferably, the support material may be alumina, in particular gamma-alumina. In this embodiment, the support material has a surface area of more than 20 $m^2/g$, preferably at least 25 $m^2/g$, more preferably at least 50 $m^2/g$, most preferably at least 75 $m^2/g$, in particular at least 100 $m^2/g$, more in particular at least 125 $m^2/g$. The support material may have a surface area of at most 1200 $m^2/g$, preferably at most 300 $m^2/g$, more preferably at most 200 $m^2/g$, most preferably at most 175 $m^2/g$.

In this embodiment, the purification absorbent may have a quantity of silver relative to the surface area of the support material (i.e., silver density) of less than 0.025 g $Ag/m^2$, preferably at most 0.01 g $Ag/m^2$, more preferably at most 0.005 g $Ag/m^2$. The purification absorbent may have a silver density of at least $1\times10^{-5}$ g $Ag/m^2$, preferably at least $5\times10^{-5}$ g $Ag/m^2$, more preferably at least $1\times10^{-4}$ g $Ag/m^2$. In this embodiment, it is preferred that the purification absorbent has a lower silver density than the silver density of the epoxidation catalyst.

In this embodiment, the purification absorbent comprises an alkali or alkaline earth metal component. Preferably, the alkali metal may be selected from sodium, potassium, lithium, rubidium, cesium, and combinations thereof, in particular sodium and potassium. Preferably, the alkaline earth metal may be selected from calcium, magnesium, strontium, barium, and combinations thereof. The alkali metal component may suitably be provided in salt or base form. Suitable alkali metal salts may include, but are not limited to, nitrates, oxalates, citrates, acetates, carbonates, and the like. Preferably, the alkali metal component may be in the form of a nitrate, hydroxide, carbonate, chloride, or bicarbonate. The alkaline earth metal component may suitably be provided in salt or base form. Suitable alkaline earth metal salts may include, but are not limited to, nitrates, oxalates, citrates, acetates, carbonates, chlorides, and the like. Preferably, the alkaline earth metal component may be in the form of a hydroxide. Without wishing to be bound by theory, it is believed that the alkali or alkaline earth metals present in the purification absorbent reduce the amount of acidic sites present on the surface of the support material which can react with a hydrocarbon such as an alkene, forming unwanted by-products in the feed.

In this embodiment, the alkali or alkaline earth metals may be present in a total quantity of at least 0.1 mmole/kg, more typically at least 1 mmole/kg, in particular at least 10 mmole/kg, more in particular at least 50 mmole/kg, most in particular at least 100 mmole/kg, calculated as the total quantity of the elements (for example sodium, potassium, rubidium, cesium, magnesium, calcium, strontium, and barium) relative to the weight of the purification absorbent. The alkali or alkaline earth metals may be present in a quantity of at most 5000 mmole/kg, preferably at most 500 mmole/kg, more preferably at most 300 mmole/kg, calculated as the total quantity of the elements relative to the weight of the purification absorbent.

In a separate embodiment, the purification absorbent may be a basic zeolite. Basic zeolites may include any basic zeolites capable of reducing bromide-containing impurities from a feed. Zeolites belong to a class of highly structured alumina silicates. Most zeolites are made artificially, but some are found as minerals in nature. The porous structure of zeolites consists of a crystal lattice in which oxygen, silicon, and aluminium atoms are placed. Commercial zeolites are categorized, depending on the structure and functionality, as P-, A-, X-, and Y-zeolites. Basic zeolites are characterized by low silicon/aluminum molar ratios and by the presence of weakly electronegative alkaline cations. Suitably, the basic zeolites have a Si:Al ratio of from 1:1 to 6:1, in particular from 1:1 to 2.5:1. Well known methods of ion exchange and impregnation may be used to prepare basic zeolites. Useful ion-exchange compounds may include alkali metal cation containing materials and alkaline earth metal cation containing materials.

In a separate embodiment, the purification absorbent may comprise an alkali metal or alkaline earth metal carbonate. Suitably, the alkali metal may include sodium, potassium, rubidium, and cesium, in particular sodium, potassium and cesium. Suitably, the alkaline earth metal may include magnesium, calcium, strontium, and barium, in particular magnesium and calcium.

In a separate embodiment, the purification absorbent may comprise silver oxide. In this embodiment, the purification absorbent may additionally comprise a support material.

In this embodiment, the support material may include natural or artificial inorganic materials, such as refractory materials, silicon carbide, clays, zeolites, charcoal, and alkaline earth metal carbonates, such as magnesium carbonate and calcium carbonate. Suitably, the refractory materials may include alumina, magnesia, zirconia, silica, and mixtures thereof. When a support material is used, the purification absorbent may be prepared using various techniques including co-mulling, impregnating, and co-precipitating methods. Such methods are well known to the skilled person.

In a separate embodiment, the purification absorbent may comprise a Group 11 metal chloride. Suitably, the Group 11 metal may be silver. In this embodiment, the purification absorbent may additionally comprise a support material. In this embodiment, the support material may include natural or artificial inorganic materials, such as refractory materials, silicon carbide, clays, zeolites, charcoal, and alkaline earth metal carbonates, such as magnesium carbonate and calcium carbonate. Suitably, the refractory materials may include alumina, magnesia, zirconia, silica, and mixtures thereof. When a support material is used, the purification absorbent may be prepared using various techniques including co-mulling, impregnating, and co-precipitating methods. Such methods are well known to the skilled person.

The epoxidation reactor vessel contains an epoxidation zone comprising an epoxidation catalyst bed. In the normal practice of this invention, a major portion of the epoxidation catalyst bed comprises epoxidation catalyst particles. By a "major portion" it is meant that the ratio of the weight of the epoxidation catalyst particles to the weight of all the particles contained in the epoxidation catalyst bed is at least 0.50, in particular at least 0.8, preferably at least 0.85, more preferably at least 0.9. Particles which may be contained in the epoxidation catalyst bed other than the epoxidation catalyst particles are, for example, inert particles; however, it is preferred that such other particles are not present in the epoxidation catalyst bed. The epoxidation catalyst bed is supported in the one or more reactor tubes by a catalyst support means arranged in the lower ends of the reactor tubes. The support means may include a screen or a spring.

The epoxidation catalyst bed may have any bed height. Suitably, the epoxidation catalyst bed may have a bed height of 100% of the length of the reactor tube, when a purification zone is not located within the reactor tubes. The epoxidation catalyst bed may suitably have a bed height of at most 95% or at most 90%, or at most 85%, or at most 80% of the length of the reactor tube. The epoxidation catalyst bed may suitably have a bed height of least 10% of the length of the reactor tube, in particular at least 25%, more in particular at least 50% of the length of the reactor tube.

The one or more reactor tubes may also contain a separate bed of particles of an inert material for the purpose of, for example, heat exchange with a feedstream. The one or more reactor tubes may also contain another such separate bed of inert material for the purpose of, for example, heat exchange with the epoxidation reaction product. Alternatively, rod-shaped metal inserts may be used in place of the bed of inert material. For further description of such inserts, reference is made to U.S. Pat. No. 7,132,555, which description is incorporated by reference.

Suitably, the temperature of the epoxidation catalyst in the epoxidation zone may be at least 150° C., in particular at least 180° C., more in particular at least 220° C. The temperature of the epoxidation catalyst bed in the epoxidation zone may be at most 325° C., in particular at most 300° C. The temperature of the epoxidation catalyst bed in the epoxidation zone may be in the range of from 180 to 325° C., preferably from 200 to 300° C.

The catalyst typically used for the epoxidation of an alkene is a catalyst comprising silver deposited on a carrier. The size and shape of the epoxidation catalyst is not critical to the invention and may be in the form of chunks, pieces, cylinders, rings, spheres, wagon wheels, tablets, and the like of a size suitable for employment in a fixed bed shell-and-tube heat exchanger reactor vessel, for example from 2 mm to 20 mm.

The carrier may be based on a wide range of materials. Such materials may be natural or artificial inorganic materials and they may include refractory materials, silicon carbide, clays, zeolites, charcoal, and alkaline earth metal carbonates, for example calcium carbonate. Preferred are refractory materials, such as alumina, magnesia, zirconia, silica, and mixtures thereof. The most preferred material is α-alumina. Typically, the carrier comprises at least 85% w, more typically at least 90% w, in particular at least 95% w α-alumina, frequently up to 99.9% w α-alumina, relative to the weight of the carrier. Other components of the α-alumina carrier may comprise, for example, silica, titania, zirconia, alkali metal components, for example sodium and/or potassium components, and/or alkaline earth metal components, for example calcium and/or magnesium components.

The surface area of the carrier may suitably be at least 0.1 $m^2/g$, preferably at least 0.3 $m^2/g$, more preferably at least 0.5 $m^2/g$, and in particular at least 0.6 $m^2/g$, relative to the weight of the carrier; and the surface area may suitably be at most 10 $m^2/g$, preferably at most 6 $m^2/g$, and in particular at most 4 $m^2/g$, relative to the weight of the carrier. "Surface area" as used herein is understood to relate to the surface area as determined by the B.E.T. (Brunauer, Emmett and Teller) method as described in Journal of the American Chemical Society 60 (1938) pp. 309-316. High surface area carriers, in particular when they are alpha alumina carriers optionally comprising in addition silica, alkali metal and/or alkaline earth metal components, provide improved performance and stability of operation.

The water absorption of the carrier may suitably be at least 0.2 g/g, preferably at least 0.25 g/g, more preferably at least 0.3 g/g, most preferably at least 0.35 g/g; and the water absorption may suitably be at most 0.85 g/g, preferably at most 0.7 g/g, more preferably at most 0.65 g/g, most preferably at most 0.6 g/g. The water absorption of the carrier may be in the range of from 0.2 to 0.85 g/g, preferably in the range of from 0.25 to 0.7 g/g, more preferably from 0.3 to 0.65 g/g, most preferably from 0.3 to 0.6 g/g. A higher water absorption may be in favor in view of a more efficient deposition of the metal and promoters, if any, on the carrier by impregnation. However, at a higher water absorption, the carrier, or the catalyst made therefrom, may have lower crush strength. As used herein, water absorption is deemed to have been measured in accordance with ASTM C20, and water absorption is expressed as the weight of the water that can be absorbed into the pores of the carrier, relative to the weight of the carrier.

The preparation of the epoxidation catalyst comprising silver is known in the art and the known methods are applicable to the preparation of the shaped catalyst particles which may be used in the practice of this invention. Methods of depositing silver on the carrier include impregnating the carrier with a silver compound containing cationic silver and/or complexed silver and performing a reduction to form metallic silver particles. For further description of such methods, reference may be made to U.S. Pat. No. 5,380,697, U.S. Pat. No. 5,739,075, EP-A-266015, and U.S. Pat. No. 6,368,998, which methods are incorporated herein by reference. Suitably, silver dispersions, for example silver sols, may be used to deposit silver on the carrier.

The reduction of cationic silver to metallic silver may be accomplished during a step in which the epoxidation catalyst is dried, so that the reduction as such does not require a separate process step. This may be the case if the silver containing impregnation solution comprises a reducing agent, for example, an oxalate, a lactate or formaldehyde.

Appreciable catalytic activity may be obtained by employing a silver content of the epoxidation catalyst of at least 10 g/kg, relative to the weight of the catalyst. Preferably, the epoxidation catalyst comprises silver in a quantity of from 50 to 500 g/kg, more preferably from 100 to 400 g/kg, for example 105 g/kg, or 120 g/kg, or 190 g/kg, or 250 g/kg, or 350 g/kg, on the same basis. As used herein, unless otherwise specified, the weight of the epoxidation catalyst is deemed to be the total weight of the catalyst including the weight of the carrier and catalytic components.

The epoxidation catalyst for use in this invention may comprise a promoter component which comprises an element selected from rhenium, tungsten, molybdenum, chromium, nitrate- or nitrite-forming compounds, and combinations thereof. Preferably the promoter component comprises, as an element, rhenium. The form in which the promoter component may be deposited onto the carrier is not material to the invention. Rhenium, molybdenum, tungsten, chromium or the nitrate- or nitrite-forming compound may suitably be provided as an oxyanion, for example, as a perrhenate, molybdate, tungstate, or nitrate, in salt or acid form.

The promoter component may typically be present in a quantity of at least 0.1 mmole/kg, more typically at least 0.5 mmole/kg, in particular at least 1 mmole/kg, more in particular at least 1.5 mmole/kg, calculated as the total quantity of the element (that is rhenium, tungsten, molybdenum and/or chromium) relative to the weight of the catalyst. The promoter component may be present in a quantity of at most 50 mmole/kg, preferably at most 10 mmole/kg, calculated as the total quantity of the element relative to the weight of the catalyst.

When the epoxidation catalyst comprises rhenium as the promoter component, the epoxidation catalyst may preferably comprise a rhenium co-promoter, as a further component deposited on the carrier. Suitably, the rhenium co-promoter may be selected from components comprising an element selected from tungsten, chromium, molybdenum, sulfur, phosphorus, boron, and combinations thereof. Preferably, the rhenium co-promoter is selected from tungsten, chromium, molybdenum, sulfur, and combinations thereof. It is particularly preferred that the rhenium co-promoter comprises, as an element, tungsten and/or sulfur.

The rhenium co-promoter may typically be present in a total quantity of at least 0.1 mmole/kg, more typically at least 0.25 mmole/kg, and preferably at least 0.5 mmole/kg, calculated as the element (i.e. the total of tungsten, chromium, molybdenum, sulfur, phosphorus and/or boron), relative to the weight of the catalyst. The rhenium co-promoter may be present in a total quantity of at most 40 mmole/kg, preferably at most 10 mmole/kg, more preferably at most 5 mmole/kg, on the same basis. The form in which the rhenium co-promoter may be deposited on the carrier is not material to the invention. For example, it may suitably be provided as an oxide or as an oxyanion, for example, as a sulfate, borate or molybdate, in salt or acid form.

The epoxidation catalyst preferably comprises silver, the promoter component, and a component comprising a further element, deposited on the carrier. Eligible further elements may be selected from the group of nitrogen, fluorine, alkali metals, alkaline earth metals, titanium, hafnium, zirconium, vanadium, thallium, thorium, tantalum, niobium, gallium and germanium and combinations thereof. Preferably the alkali metals are selected from lithium, potassium, rubidium and cesium. Most preferably the alkali metal is lithium, potassium and/or cesium. Preferably the alkaline earth metals are selected from calcium, magnesium and barium. Typically, the further element is present in the epoxidation catalyst in a total quantity of from 0.01 to 500 mmole/kg, more typically from 0.05 to 100 mmole/kg, calculated as the element, relative to the weight of the catalyst. The further elements may be provided in any form. For example, salts of an alkali metal or an alkaline earth metal are suitable. For example, lithium compounds may be lithium hydroxide or lithium nitrate.

Preferred amounts of the components of the epoxidation catalysts are, when calculated as the element, relative to the weight of the catalyst:

silver from 10 to 500 g/kg, rhenium from 0.01 to 50 mmole/kg, if present, the further element or elements, if present, each from 0.1 to 500 mmole/kg, and, the rhenium co-promoter from 0.1 to 30 mmole/kg, if present.

As used herein, the quantity of alkali metal present in the catalyst or absorbent is deemed to be the quantity insofar as it can be extracted from the catalyst or absorbent with de-ionized water at 100° C. The extraction method involves extracting a 10-gram sample of the catalyst or absorbent three times by heating it in 20 ml portions of de-ionized water for 5 minutes at 100° C. and determining in the combined extracts the relevant metals by using a known method, for example atomic absorption spectroscopy.

As used herein, the quantity of alkaline earth metal present in the catalyst or absorbent is deemed to be the quantity insofar as it can be extracted from the catalyst or absorbent with 10% w nitric acid in de-ionized water at 100° C. The extraction method involves extracting a 10-gram sample of the catalyst or absorbent by boiling it with a 100 ml portion of 10% w nitric acid for 30 minutes (1 atm., i.e. 101.3 kPa) and determining in the combined extracts the relevant metals by using a known method, for example atomic absorption spectroscopy. Reference is made to U.S. Pat. No. 5,801,259, which is incorporated herein by reference.

Although the present epoxidation process may be carried out in many ways, it is preferred to carry it out as a gas phase process, i.e. a process in which an epoxidation reaction feed is contacted in the gas phase with the epoxidation catalyst to yield an epoxidation reaction product comprising an alkylene oxide. The term "epoxidation reaction product", as used herein, is understood to refer to the fluid exiting from the outlet of the epoxidation reactor vessel. Generally the process is carried out as a continuous process.

The epoxidation feed components include an alkene, oxygen, and an epoxidation recycle gas. Additional epoxidation feed components may include an organic chloride reaction modifier, a nitrogen-containing reaction modifier, a saturated hydrocarbon, and an inert dilution gas.

The quantity of alkene present in the epoxidation feed may be selected within a wide range. Typically, the quantity of alkene present in the epoxidation feed may be at most 80 mole-%, relative to the total epoxidation feed. Preferably, it may be in the range of from 0.5 to 70 mole-%, in particular from 1 to 60 mole-%, more in particular from 15 to 40 mole-%, on the same basis.

The present epoxidation process may be air-based or oxygen-based, see "Kirk-Othmer Encyclopedia of Chemical Technology", $3^{rd}$ edition, Volume 9, 1980, pp. 445-447. In the air-based process, air or air enriched with oxygen is employed as the source of the oxidizing agent while in the oxygen-based processes high-purity (at least 95 mole-%) oxygen or very high purity (at least 99.5 mole-%) oxygen is employed as the source of the oxidizing agent. Reference may be made to U.S. Pat. No. 6,040,467, incorporated by reference, for further description of oxygen-based processes. Presently most epoxidation plants are oxygen-based and this is a preferred embodiment of the present invention.

The quantity of oxygen present in the epoxidation feed may be selected within a wide range. However, in practice, oxygen is generally applied in a quantity which avoids the flammable regime. Oxygen may be present in a quantity of at least 0.5 mole-%, relative to the total epoxidation feed, in particular at least 1 mole-%, more in particular at least 2 mole-%, most in particular at least 5 mole-%, relative to the total epoxidation feed. Oxygen may be present in a quantity of at most 25 mole-%, relative to the total epoxidation feed, in particular at most 20 mole-%, more in particular at most 15 mole-%, most in particular at most 12 mole-%, relative to the total epoxidation feed In order to remain outside the flammable regime, the quantity of oxygen in the epoxidation feed may be lowered as the quantity of the alkene is increased. The actual safe operating ranges depend, along with the epoxidation feed composition, also on the reaction conditions such as the reaction temperature and the pressure.

An organic chloride reaction modifier may be present in the epoxidation feed for increasing the selectively, suppressing the undesirable oxidation of alkene or alkylene oxide to carbon dioxide and water, relative to the desired formation of alkylene oxide.

Preferred organic chloride reaction modifiers are chlorohydrocarbons. More preferably they are selected from the group of methyl chloride, ethyl chloride, ethylene dichloride, vinyl chloride or a mixture thereof. Most preferred organic chloride reaction modifiers are ethyl chloride and ethylene dichloride.

The epoxidation feed may include a nitrogen-containing reaction modifier. Nitrogen oxides, organic nitro compounds such as nitromethane, nitroethane, and nitropropane, hydrazine, hydroxylamine or ammonia may be employed. It is frequently considered that under the operating conditions of alkene epoxidation the nitrogen containing reaction modifiers are precursors of nitrates or nitrites, i.e. they are so-called nitrate- or nitrite-forming compounds (cf. e.g. EP-A-3642 and U.S. Pat. No. 4,822,900, which are incorporated herein by reference).

Suitable nitrogen oxides are of the general formula $NO_x$ wherein x is in the range of from 1 to 2.5, and include for example $NO$, $N_2O_3$, $N_2O_4$, and $N_2O_5$. Suitable organic nitrogen compounds are nitro compounds, nitroso compounds, amines, nitrates and nitrites, for example nitromethane, 1-nitropropane or 2-nitropropane.

The reaction modifiers are generally effective when used in small quantities in the epoxidation feed. The nitrogen-containing reaction modifier may be present in a quantity of at most $500 \times 10^{-4}$ mole-%, relative to the total epoxidation feed, in particular at most $400 \times 10^{-4}$ mole-%, more in particular at most $300 \times 10^{-4}$ mole-%, relative to the total epoxidation feed. The nitrogen-containing reaction modifier may be present in a quantity of at least $5 \times 10^{-4}$ mole-%, relative to the total epoxidation feed, in particular at least $10 \times 10^{-4}$ mole-%, more in particular at least $50 \times 10^{-4}$ mole-%, relative to the total epoxidation feed. When a nitrogen-containing reaction modifier is utilized in the epoxidation feed, the organic chloride may be present in a quantity of at most $500 \times 10^{-4}$ mole-%, relative to the total epoxidation feed, in particular at most $400 \times 10^{-4}$ mole-%, more in particular at most $300 \times 10^{-4}$ mole-%, relative to the total epoxidation feed. When a nitrogen-containing reaction modifier is utilized in the epoxidation feed, the organic chloride reaction modifier may be present in a quantity of at least $5 \times 10^{-4}$ mole-%, relative to the total epoxidation feed, in particular at least $10 \times 10^{-4}$ mole-%, more in particular at least $50 \times 10^{-4}$ mole-%, relative to the total epoxidation feed. When the only reaction modifier used in the epoxidation feed is an organic chloride, the organic chloride may be present in a quantity of at most $50 \times 10^{-4}$ mole-%, relative to the total epoxidation feed, in particular at most $20 \times 10^{-4}$ mole-%, more in particular at most $10 \times 10^{-4}$ mole-%, relative to the total epoxidation feed. When the only reaction modifier used in the epoxidation feed is an organic chloride, the organic chloride reaction modifier may be present in a quantity of at least $5 \times 10^{-5}$ mole-%, relative to the total epoxidation feed, in particular at least $7.5 \times 10^{-5}$ mole-%, more in particular at least $1 \times 10^{-4}$ mole-%, relative to the total epoxidation feed.

The epoxidation feed also contains a recycle gas. The epoxidation reaction product comprises the alkylene oxide, unreacted alkene, unreacted oxygen, and optionally, an organic chloride reaction modifier, a nitrogen-containing reaction modifier, a saturated hydrocarbon, an inert dilution gas, and other reaction by-products such as carbon dioxide and water. The reaction product is passed through one or more separation systems, such as an alkylene oxide absorber and a carbon dioxide absorber, so the unreacted alkene and oxygen as well as other components such as the dilution gases and reaction modifier may be recycled to the reactor system. The recycle gas loop comprises interconnecting pipework between the alkylene oxide absorber and the epoxidation reactor vessel and optionally includes a carbon dioxide absorber, heat exchangers, compressors, and water removal ("knock-out") vessels in the recycle gas loop. Carbon dioxide is a by-product in the epoxidation process. However, carbon dioxide generally has an adverse effect on the catalyst activity. Typically, a quantity of carbon dioxide in the epoxidation feed in excess of 25 mole-%, in particular in excess of 10 mole-%, relative to the total epoxidation feed, is avoided. A quantity of carbon dioxide of less than 3 mole-%, preferably less than 2 mole-%, more preferably less than 1 mole-%, relative to the total epoxidation feed, may be employed. Under commercial operations, a quantity of carbon dioxide of at least 0.1 mole-%, in particular at least 0.2 mole-%, relative to the total epoxidation feed, may be present in the epoxidation feed.

The epoxidation feed may also comprise a saturated hydrocarbon. The saturated hydrocarbon may be selected from methane, ethane, propane, butane, pentane, hexane, heptane, octane, nonane, decane, undecane, dodecane and mixtures thereof. In particular, the saturated hydrocarbon may be selected from methane, ethane, propane, and mixtures thereof, preferably methane. Saturated hydrocarbons are common dilution gases in an epoxidation process.

Saturated hydrocarbons, in particular methane, ethane and mixtures thereof, more in particular methane, may be present in a quantity of at most 80 mole-%, relative to the total epoxidation feed, in particular at most 75 mole-%, more in particular at most 65 mole-%, on the same basis. The saturated hydrocarbons may be present in a quantity of at least 1 mole-%, preferable at least 10 mole-%, more preferably at least 30 mole-%, most preferably at least 40 mole-%, on the same basis. Saturated hydrocarbons may be added to the epoxidation feed in order to increase the oxygen flammability limit.

Inert dilution gases, for example nitrogen, helium or argon, may be present in the epoxidation feed in a quantity of from 30 to 90 mole-%, typically from 40 to 80 mole-%, relative to the total epoxidation feed.

The epoxidation process is preferably carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is a gas phase process involving a packed catalyst bed, the GHSV is in the range of from 1500 to 10000 Nl/(l.h). Preferably, the process is carried out at a work rate in the range of from 0.5 to 10 kmole alkylene oxide produced per $m^3$ of catalyst per hour, in particular 0.7 to 8 kmole alkylene oxide produced per $m^3$ of catalyst per hour, for example 5 kmole alkylene oxide produced per $m^3$ of catalyst per hour. As used herein, the work rate is the amount of the alkylene oxide produced per unit volume of catalyst per hour and the selectivity is the molar quantity of the alkylene oxide formed relative to the molar quantity of the alkene converted. As used herein, the activity is a measurement of the temperature required to achieve a particular ethylene oxide production level. The lower the temperature, the better the activity.

Preferably, water is removed from the epoxidation reaction product before it is supplied to the alkylene oxide absorber. Additionally, contaminants are preferably removed from the epoxidation reaction product before it is supplied to the alkylene oxide absorber. Possible contaminants include acids, esters, aldehydes, acetals and organic halides. Preferably, the lean absorbent comprises at least 50 wt % (weight percent) alkylene carbonate and less than 10 wt % water. By restricting the amount of water supplied to the alkylene oxide absorber, there is a reduced requirement to remove water from any gases that are recirculated from the alkylene oxide absorber to the epoxidation reactor, and there is more opportunity to use bromide-containing carboxylation catalysts that function most effectively in substantially non-aqueous environments.

A preferred method of removing water and optionally contaminants is quenching, preferably by contacting the epoxidation reaction product with a recirculating aqueous solution that is preferably cooled or chilled, e.g. less than 20° C. Lowering the quench temperature will reduce the water content in the gas feed to the alkylene oxide absorber. Quenching is preferably carried out in the same vessel as the alkylene oxide absorber. A portion of the recirculating aqueous solution may be withdrawn as a bleed stream from the quench section, and any alkylene oxide in the bleed stream may be recovered by conventional methods. In one embodiment, substances, e.g. bases such as sodium hydroxide, are added to the recirculating aqueous solution to enhance removal of contaminants. After quenching, the epoxidation reaction product may be reheated before it is supplied to the alkylene oxide absorber, preferably by heat integration with the hot epoxidation reaction product from the epoxidation reactor.

Another method of removing water and optionally contaminants is to cool the gas stream using heat exchangers, causing condensation of water that can thereafter be removed. Most preferably water and optionally contaminants are removed using both quenching and cooling by heat exchangers. If the water content in the gas to the alkylene oxide absorber remains high, the water content in the absorber may optionally be reduced by supplying hydrolysis catalyst to the alkylene oxide absorber (and/or to any finishing reactor(s)), thereby promoting reaction of any water that is present with alkylene oxide to form alkylene glycol.

The epoxidation reaction product is supplied to an alkylene oxide absorber. The alkylene oxide absorber preferably comprises a column of vertically stacked trays or a packed column The trays or the packed column provide a surface area for the absorbent and epoxidation reaction product to come into contact, facilitating mass transfer between the two phases. Additionally, trays provide considerable liquid volume in which the liquid phase reaction can occur. In the embodiment wherein the alkylene oxide absorber comprises a series of vertically stacked trays, gases can pass upwards through the trays and liquid can flow downwards from tray to tray. Preferably the column comprises at least 20 trays, more preferably at least 30 trays. Preferably the column comprises less than 70 trays. More trays increase the absorption ability and reaction volume of the column, but adding additional trays increases expense. In the embodiment wherein the alkylene oxide absorber comprises a packed column, conventional packing such as structured packing, random packing and catalytic distillation internals may be used.

The epoxidation reaction product is preferably supplied at the bottom of the alkylene oxide absorber. If the alkylene oxide absorber comprises a column of vertically stacked trays, the epoxidation reaction product is preferably supplied below the bottom tray in the column. If the alkylene oxide absorber comprises a packed column, the epoxidation reaction product is preferably supplied below the packing material.

Lean absorbent is supplied to the alkylene oxide absorber and contacted with the epoxidation reaction product in the alkylene oxide absorber and fat absorbent (comprising components absorbed from the epoxidation reaction product including alkylene carbonate) is withdrawn from the alkylene oxide absorber. In one embodiment, the lean absorbent is supplied at the top of the alkylene oxide absorber. If the alkylene oxide absorber comprises a column of vertically stacked trays, the lean absorbent is preferably supplied to the uppermost tray in the absorption column. If the alkylene oxide absorber comprises a packed column, the lean absorbent is preferably supplied above the packing material. In another embodiment, the lean absorbent is supplied such that there are trays or packing above the point at which the lean absorbent is supplied to the alkylene oxide absorber. In this embodiment, additional lean absorbent that has been cooled can be supplied at the top of the alkylene oxide absorber to absorb alkylene oxide or contaminants in the top of the alkylene oxide absorber.

The lean absorbent comprises at least 50 wt % alkylene carbonate and comprises less than 10 wt % water. If the process of the invention is for the preparation of ethylene glycol, the preferred alkylene carbonate is ethylene carbonate. If the process of the invention is for the preparation of propylene glycol, the preferred alkylene carbonate is propylene carbonate. The lean absorbent preferably comprises at least 60 wt % alkylene carbonate and more preferably comprises at least 70 wt % alkylene carbonate. The lean absorbent preferably comprises less than 3 wt % water and more preferably comprises less than 2 wt % water Minimising the amount of water is particularly important if the bromide-containing carboxylation catalyst is water sensitive. The lean absorbent may also comprise alkylene glycol.

The epoxidation reaction product is contacted with lean absorbent in the alkylene oxide absorber in the presence of one or more bromide-containing carboxylation catalyst. The bromide-containing carboxylation catalysts may be homogeneous and/or heterogeneous. When heterogeneous catalysts are used, the catalyst is contained in the vertically stacked trays or in the packing of a packed column.

The bromide-containing carboxylation catalyst may be a homogenous catalyst. Suitable homogenous bromide-containing catalysts that are known to promote carboxylation may include alkali metal bromides such as potassium bromide, zinc bromide with quaternary ammonium or phosphonium halides (for example n-butyl ammonium halides), imidazolium bromide salts, indium bromide, lead bromide, and halogenated organic phosphonium or ammonium salts such as triphenyl-propylphosphonium bromide, tetraethylammonium bromide, tetramethylammonium bromide, benzylriethylammonium bromide and tetrabutyllammonium bromide.

The bromide-containing carboxylation catalyst may be a heterogeneous bromide-containing catalysts. Suitable heterogeneous bromide-containing catalysts that promote carboxylation are preferably based upon solid supports such as ion exchange resins, silica, polysiloxane, polyvinylpyridine or polystyrene, for example quaternary ammonium and quaternary phosphonium bromides immobilized on silica, quaternary ammonium and quaternary phosphonium bromides bound to insoluble polystyrene beads. Preferably, a solid support such as an ion exchange resin is functionalized with a quaternary ammonium or phosphonium halide (for example bromide) and is used in combination with a metal bromide co-catalyst such as a zinc bromide. Alternatively, quaternary ammonium and quaternary phosphonium bromides may be immobilized on silica or bound to insoluble polystyrene beads. Alternatively, metal bromide salts such as zinc bromide may be supported on solid supports such as polyvinylpyridine, polyvinylpyrrolidine and chitosan. The heterogeneous catalyst is preferably integrated into the alkylene oxide absorber using reactive distillation packing such as M-SERIES™ packing from CDTech, KATAPAK™ SP packing from Sulzer Chemtech, KATAMAX™ packing from Koch or MULTIPAK™ packing from Montz.

The most preferred catalyst will have high activity for the carboxylation reaction when present in a reaction medium consisting predominantly of alkylene carbonate and comprising very little water. The catalyst will preferably be stable during the reaction.

In an embodiment, a homogeneous non-bromide-containing carboxylation catalyst may also be present in the alkylene oxide absorber. Such catalysts known to promote carboxylation in substantially non-aqueous media may include, but are not limited to, zinc halides (especially zinc iodide) with quaternary ammonium or phosphonium halides (for example n-butyl ammonium halides), ionic liquids such as imidazolium salts, pyridine derivatives, indium halides (for example indium chloride and indium iodide), lead halides (for example lead iodide) and polyoxometalates. Other homogeneous carboxylation catalysts known to the skilled person include alkali metal halides such as potassium iodide, and halogenated organic phosphonium or ammonium salts such as tributylmethylphosphonium iodide, tetrabutylphosphonium iodide, triphenylmethylphosphonium iodide, triphenylbenzylphosphonium chloride, and tributylmethylammonium iodide.

In an embodiment, a heterogeneous non-bromide-containing carboxylation catalyst may also be present in the alkylene oxide absorber. Such catalysts known to promote carboxylation in substantially non-aqueous media may include, but are not limited to, a solid support such as an ion exchange resin is functionalised with a quaternary ammonium or phosphonium halide and is used in combination with a metal salt co-catalyst such as a zinc halide (for example zinc iodide). Alternatively quaternary ammonium and quaternary phosphonium halides (for example iodides) may be immobilized on silica or bound to insoluble polystyrene beads. Alternatively metal salts such as zinc halides (for example zinc iodide) may be supported on solid supports such as polyvinylpyridine, polyvinylpyrrolidine and chitosan.

It has been found that gaseous bromide-containing impurities are formed which exit the alkylene oxide absorber with the recycle gas stream. The gaseous bromide-containing impurities generated may include inorganic bromide compounds and organic bromide compounds. Bromide-containing impurities such as these can poison the epoxidation catalyst in the epoxidation reactor. Contacting the recycle gas with a purification absorbent capable of reducing the quantity of bromide-containing impurities can reduce the quantity of bromide-containing impurities in the recycle gas and thus improve the performance of the epoxidation catalyst, in particular selectivity, activity, and the duration of time the epoxidation catalyst remains in the epoxidation reactor before having to exchange the catalyst with a fresh epoxidation catalyst.

The lean absorbent is supplied to the alkylene oxide absorber at a temperature greater than 60° C. Supplying the lean absorbent at a temperature greater than 60° C. promotes carboxylation in the absorber and ensures that the alkylene carbonate that is produced does not solidify. Solidification is a common problem for ethylene carbonate, which has a melting point of 34° C. Preferably the lean absorbent is supplied at a temperature greater than 65° C., more preferably at a temperature greater than 70° C., even more preferably at a temperature greater than 80° C. and most preferably at a temperature between 90° C. and 250° C.

The epoxidation reaction product is preferably supplied to the alkylene oxide absorber at a temperature greater than 60° C. Preferably the epoxidation reaction product is supplied at a temperature greater than 65° C., more preferably at a temperature greater than 70° C., even more preferably at a temperature greater than 80° C. and most preferably at a temperature between 90° C. and 200° C.

The temperature in the alkylene oxide absorber is affected by the temperature of the epoxidation reaction product and lean absorbent supplied to the alkylene oxide absorber. Additionally, because the carboxylation reaction is exothermic, it is preferred to control the temperature in the alkylene oxide absorber by withdrawing absorbent from the column, cooling and returning the absorbent to the column. The temperature in the alkylene oxide absorber is preferably controlled such that it is greater than 80° C., more preferably greater than 90° C. and is preferably less than 250° C. This temperature promotes the carboxylation reaction and ensures that the alkylene carbonate that is produced does not solidify.

The pressure in the alkylene oxide absorber is preferably from 1 to 4M Pa, more preferably from 2 to 3 MPa. The preferred pressure is a compromise between lower pressures that require less expensive equipment (e.g. equipment having thinner walls) and higher pressures that increase absorption and reduce the volumetric flow of the gas, thereby reducing the size of equipment and piping.

The alkylene oxide and carbon dioxide in the epoxidation reaction product are absorbed into the absorbent. The bromide-containing carboxylation catalyst promotes carboxylation and preferably at least 60% of the alkylene oxide entering the alkylene oxide absorber is converted to alkylene carbonate in the alkylene oxide absorber. More preferably at least 80% of the alkylene oxide entering the alkylene oxide absorber is converted in the alkylene oxide absorber.

The epoxidation reaction product that is supplied to the alkylene oxide absorber comprises carbon dioxide. It is possible that the epoxidation reaction product may contain insufficient carbon dioxide to achieve desired levels of carboxylation. This is likely to be the case when using a freshly prepared epoxidation catalyst. An additional source of carbon dioxide is preferably supplied to the alkylene oxide absorber, e.g. carbon dioxide from a carbon dioxide recovery unit or, at start-up, carbon dioxide from an external source. The molar ratio of the total amount of carbon dioxide supplied to the alkylene oxide absorber to the amount of alkylene oxide supplied to the alkylene oxide absorber is preferably between 5:1 and 1:3, more preferably between 3:1 and 4:5. A higher quantity of carbon dioxide improves conversion to alkylene carbonate. However, a higher quantity of carbon dioxide also requires either additional removal capacity for carbon dioxide in the process, which can be costly, or operating the epoxidation catalyst at higher carbon dioxide concentration which adversely affects the epoxidation catalyst performance.

Gases that are not absorbed in the alkylene oxide absorber are preferably partially or entirely supplied to a carbon dioxide absorption column wherein the carbon dioxide is at least partially absorbed by a recirculating absorbent stream. Gases that are not absorbed by the recirculating absorbent stream are preferably recombined with any gases bypassing the carbon dioxide absorption column and are recycled to the epoxidation reactor. Because the process of the present invention achieves significant reaction of alkylene oxide and carbon dioxide in the alkylene oxide absorber, carbon dioxide is effectively captured in the alkylene oxide absorber, so the quantity of carbon dioxide in the gases leaving the alkylene oxide absorber is low, reducing the need for carbon dioxide removal apparatus. In one embodiment of the invention, the amount of carbon dioxide leaving the alkylene oxide absorber in a gas stream may be sufficiently low that there is no requirement for a carbon dioxide absorption column for recovery of carbon dioxide.

Fat absorbent is withdrawn from the alkylene oxide absorber, preferably by withdrawing liquid from the bottom of the alkylene oxide absorber.

In one embodiment of the invention, a portion or all of the fat absorbent from the alkylene oxide absorber is supplied to one or more finishing reactors in a finishing zone before it is supplied to the one or more hydrolysis reactors in a hydrolysis zone. Supply to one or more finishing reactors is preferred if a significant quantity (e.g. at least 1%) of alkylene oxide supplied to the alkylene oxide absorber is not converted to alkylene carbonate in the alkylene oxide absorber. Conversely, if the majority (e.g. greater than 90%) of alkylene oxide supplied to the alkylene oxide absorber is converted to alkylene carbonate in the alkylene oxide absorber, then one or more finishing reactors may not be required and the equipment used in the process is thereby reduced. (The decision whether to employ one or more finishing reactors is most difficult in the region where from 90 to 99% of alkylene oxide supplied to the alkylene oxide absorber is converted to alkylene carbonate in the alkylene oxide absorber. In this range, a number of different factors, including costs and product quality requirements, are likely to be considered by the skilled person when considering whether to use one or more finishing reactors.) To maximise conversion of alkylene oxide in the alkylene oxide absorber, spraying nozzles can be employed in the bottom section of the alkylene oxide absorber, to disperse carbon dioxide and promote carboxylation. The one or more finishing reactors preferably include a plug flow reactor. In the one or more finishing reactors, further carboxylation of alkylene oxide occurs and preferably at least 50 wt % of alkylene oxide entering the finishing reactor is converted to alkylene carbonate in the finishing reactor, more preferably at least 90 wt %, most preferably at least 95%. The finishing reactor contains carboxylation catalyst. If a homogeneous catalyst is used in the alkylene oxide absorber, then the fat absorbent will comprise carboxylation catalyst and there is no requirement to add additional catalyst to the finishing reactor. However, in the embodiment wherein a heterogeneous catalyst is used in the alkylene oxide absorber it is preferred to incorporate a bed of heterogeneous catalyst in the finishing reactor, most preferably the same catalyst as is used in the absorber. Preferably additional carbon dioxide is supplied to the finishing reactor or to the fat absorbent after it has been withdrawn from the alkylene oxide absorber and before it is supplied to the finishing reactor.

A portion of the fat absorbent from the alkylene oxide absorber and from any additional finishing reactors is supplied to one or more hydrolysis reactors. Preferably 1-50 wt % of the fat absorbent is supplied to the hydrolysis reactor, most preferably 2-20 wt % is supplied to the hydrolysis reactor. Preferably the remainder of the fat absorbent is recycled to the alkylene oxide absorber as the lean absorbent. If there is more than one hydrolysis reactor it is preferred that the hydrolysis reactors are connected in series, i.e. the portion of fat absorbent must pass through each hydrolysis reactor sequentially.

The portion of fat absorbent that results from the alkylene oxide absorber and from any additional finishing reactors must be split into at least two portions before any of the fat absorbent is supplied to the one or more hydrolysis reactors. Additionally the fat absorbent may undergo removal of light ends and/or removal of a homogeneous carboxylation catalyst before it is supplied to the one or more hydrolysis reactors. (Light ends are gases such as the alkene, and also ballast gases such as methane, that are present in the epoxidation reaction product, are absorbed into the lean absorbent in the alkylene oxide absorber and are therefore present in the fat absorbent.)

In a preferred method that can be used to accomplish splitting of the fat absorbent into two portions, removal of light ends and removal of a homogeneous carboxylation catalyst, the fat absorbent is supplied to a flash vessel. The flash vessel can be at a pressure from 0.01 to 2 MPa, preferably from 0.1 to 1 MPa, most preferably from 0.1 to 0.5 MPa. Light ends removed using the flash vessel are preferably recirculated to the alkylene oxide absorber, and may be supplied to the bottom of the alkylene oxide absorber. Recirculating the light ends to the alkylene oxide absorber increases the efficiency of the process because light ends, comprising alkene, are recovered and are not lost when carbon dioxide is removed from the process in a carbon dioxide bleed stream. A portion of the alkylene carbonate in the fat absorbent is flashed, subsequently condensed, and supplied to the one or more hydrolysis reactors. Remaining fat absorbent, which may contain homogeneous carboxylation catalyst is preferably recycled to the alkylene oxide absorber as the lean absorbent.

In an alternative method that can be used to accomplish splitting of the fat absorbent into a portion to be supplied to the one or more hydrolysis reactors and another portion (that is preferably recycled to the alkylene oxide absorber), the fat absorbent undergoes a liquid phase splitting. With this method, there is no removal of light ends with catalyst separation, so light ends are sent to the hydrolysis reactor as part of the fat absorbent. In this method, light ends are preferably removed from the hydrolysis reactor and are recycled to the alkylene oxide absorber.

In a yet further method, the light ends are removed using a flash vessel and preferably recycled, and the remaining fat absorbent subsequently undergoes a liquid phase splitting.

Water is supplied to the one or more hydrolysis reactors. The molar ratio of water to alkylene carbonate entering the reactor is preferably in the range of 2:1 to 1:2, most preferably about 1:1. If there is more than one hydrolysis reactor, water can be supplied directly to the first hydrolysis reactor only (so water is supplied to the subsequent hydrolysis reactors via the first hydrolysis reactor), or alternatively water can be supplied directly to the first hydrolysis reactor and to one or more subsequent hydrolysis reactors. The water is preferably supplied as steam.

The fat absorbent is contacted with water in the presence of one or more hydrolysis catalysts. In one embodiment, the one or more hydrolysis catalysts are homogeneous catalysts that are supplied to the one or more hydrolysis reactors. Homogeneous catalysts that are known to promote hydrolysis include basic alkali metal salts such as potassium carbonate, potassium hydroxide and potassium bicarbonate, or alkali metal metalates such as potassium molybdate. In another embodiment, the one or more hydrolysis catalysts are heterogeneous catalysts and are preferably contained in a fixed bed in the one or more hydrolysis reactors. Heterogeneous catalysts that promote hydrolysis include metalates immobilised on solid supports, for example molybdates, vanadates or tungstates immobilised on ion exchange resins containing quaternary ammonium or quaternary phosphonium groups, or basic anions such as bicarbonate ions immobilised on solid supports, for example bicarbonate immobilised on ion exchange resins containing quaternary ammonium or quaternary phosphonium groups.

In one embodiment of the invention, at least one of the one or more hydrolysis reactors is a baffled reactor, wherein the baffled reactor has at least four compartments, the compartments are formed by internal baffles and the internal baffles provide a sinuous route for reaction fluid through the reactor. Optionally steam is injected into the baffled reactor.

Carbon dioxide will be produced in the one or more hydrolysis reactors and is preferably separated from the product stream as it leaves the one or more hydrolysis reactors and at least partially recycled to the alkylene oxide absorber and/or to one or more finishing reactors.

The temperature in the one or more hydrolysis reactors is typically from 80 to 200° C., preferably from 100 to 180° C. The pressure in the one or more hydrolysis reactors is typically from 0.1 to 3 MPa. Higher pressure can enable recycling of carbon dioxide to the absorption column and finishing reactor without the need for compression.

The product stream from the one or more hydrolysis reactors is supplied to a dehydrator in a dehydration zone. The stream that is supplied to the dehydrator preferably comprises very little alkylene oxide or alkylene carbonate, i.e. most of the alkylene oxide or alkylene carbonate has been converted to alkylene glycol prior to supply to the dehydrator column. Preferably the molar ratio of alkylene glycol to alkylene oxide and alkylene carbonate (combined) in the stream supplied to the dehydrator column is greater than 90:10, more preferably greater than 95:5, most preferably greater than 99:1. The dehydrator is preferably one or more columns, including at least one vacuum column, preferably operating at a pressure of less than 0.05 MPa, more preferably less than 0.025 MPa and most preferably about 0.0125 MPa.

If one or more homogeneous hydrolysis catalyst(s) are used in the one or more hydrolysis reactors, or if one or more homogeneous carboxylation catalyst(s) are used in the alkylene oxide absorber and not separated from the fat absorbent prior to supply to the one or more hydrolysis reactors, then the homogeneous catalyst(s) may be removed from the product stream from the one or more hydrolysis reactors or alternatively from the dehydrated product stream from the dehydrator. In one embodiment, the product stream from the one or more hydrolysis reactors is supplied to a flash vessel to separate the homogeneous catalyst(s) (which are preferably recycled to the alkylene oxide absorber or to the one or more hydrolysis reactors) and is subsequently supplied to a dehydrator. In another embodiment, the dehydrated product stream from the dehydrator is supplied to a flash vessel to separate the homogeneous catalyst(s) (which are preferably recycled to the alkylene oxide absorber or to the one or more hydrolysis reactors) and then is subsequently purified to remove impurities.

The dehydrated product stream from the dehydrator is purified in an alkylene glycol purification zone to remove impurities and provide a purified alkylene glycol product stream. The alkylene glycol purification zone contains one or more purification columns.

FIG. 1:

FIG. 1 shows a preferred embodiment of the process of the invention. Ethylene, oxygen, methane and organic chloride reaction modifier (for example ethyl chloride) are supplied to the recycle gas at (1). A purification zone (45) containing an absorbent capable of reducing the quantity of bromide-containing impurities is located in the recycle gas loop downstream from the addition of ethylene, oxygen, methane and reaction modifier and upstream from the product/feed heat exchanger. In the ethylene oxide reactor (2), the ethylene and oxygen react, providing a gas composition comprising ethylene, oxygen, methane, ethylene oxide, moderator and carbon dioxide, which is cooled and supplied to the quench (4), below the bottom tray of the quench section. The quenched gas is reheated and fed to the ethylene oxide absorber column (3) below the bottom tray or below the packing material. Optionally, additional carbon dioxide from the carbon dioxide recovery section (7) or hydrolysis reactor (13) may also be supplied to the ethylene oxide absorber (3) or may be mixed with the gases before supply to the ethylene oxide absorber. Lean absorbent comprising greater than 70 wt % ethylene carbonate, less than 2 wt % water and a homogeneous carboxylation catalyst are supplied (5) at the top of the ethylene oxide absorber column (3). The lean absorbent is supplied at a temperature of 90° C. In the ethylene oxide absorber, ethylene oxide and carbon dioxide are absorbed into the lean absorbent and react to provide ethylene carbonate. The gases that are not absorbed in ethylene oxide absorber (3) are partially or entirely supplied to carbon dioxide recovery section (7) where carbon dioxide is removed from the gas. The recovered carbon dioxide stream (8) can partially or entirely be recirculated to the ethylene oxide absorber (3), directly or by mixing with the gas feed. The gas from the ethylene oxide absorber (3), the gas from carbon dioxide recovery section (7) and the recombined gas stream fed to the reactor (2) can be cooled to reduce the water content. The liquid knocked out of the gas stream can optionally be recirculated to the ethylene oxide absorber column (3).

Fat absorbent is withdrawn (6) from the ethylene oxide absorber bottom and is supplied to a finishing reactor (20). The fat absorbent stream is then split (11) and one portion is supplied to a flash vessel (9). The homogeneous carboxylation catalyst is separated in the flash vessel, is withdrawn from the flash vessel, and is combined with the portion of fat absorbent that was not supplied to the flash vessel, before being recirculated to the absorber as the lean absorbent (5). A light ends stream (10) is withdrawn after the flash vessel and can be recirculated to the ethylene oxide absorber (3) directly or by mixing with the gas feed. The fat absorbent stream is fed to heat exchanger (12) and is subsequently supplied to a hydrolysis reactor (13).

Steam (19) and homogeneous hydrolysis catalyst (17) are supplied to the hydrolysis reactor (13). In the hydrolysis reactor (13), ethylene carbonate and water react to give monoethylene glycol. The carbon dioxide gas released (14) can be recycled to the ethylene oxide absorber (3) directly, or by mixing with the ethylene oxide absorber feed, or can be totally or partially bled. The product stream from the hydrolysis reactor (13) is supplied to a dehydrator (15) where water is removed. The dehydrated product stream is withdrawn from the dehydrator (15) and supplied to the monoethylene glycol (MEG) purification column (16). A solution comprising the hydrolysis catalyst dissolved in glycols (17) is withdrawn from the bottom of the MEG purification column (16) and is recycled to the hydrolysis reactor (13). Monoethylene glycol product (18) is withdrawn from the MEG purification column top section.

Figure 2:
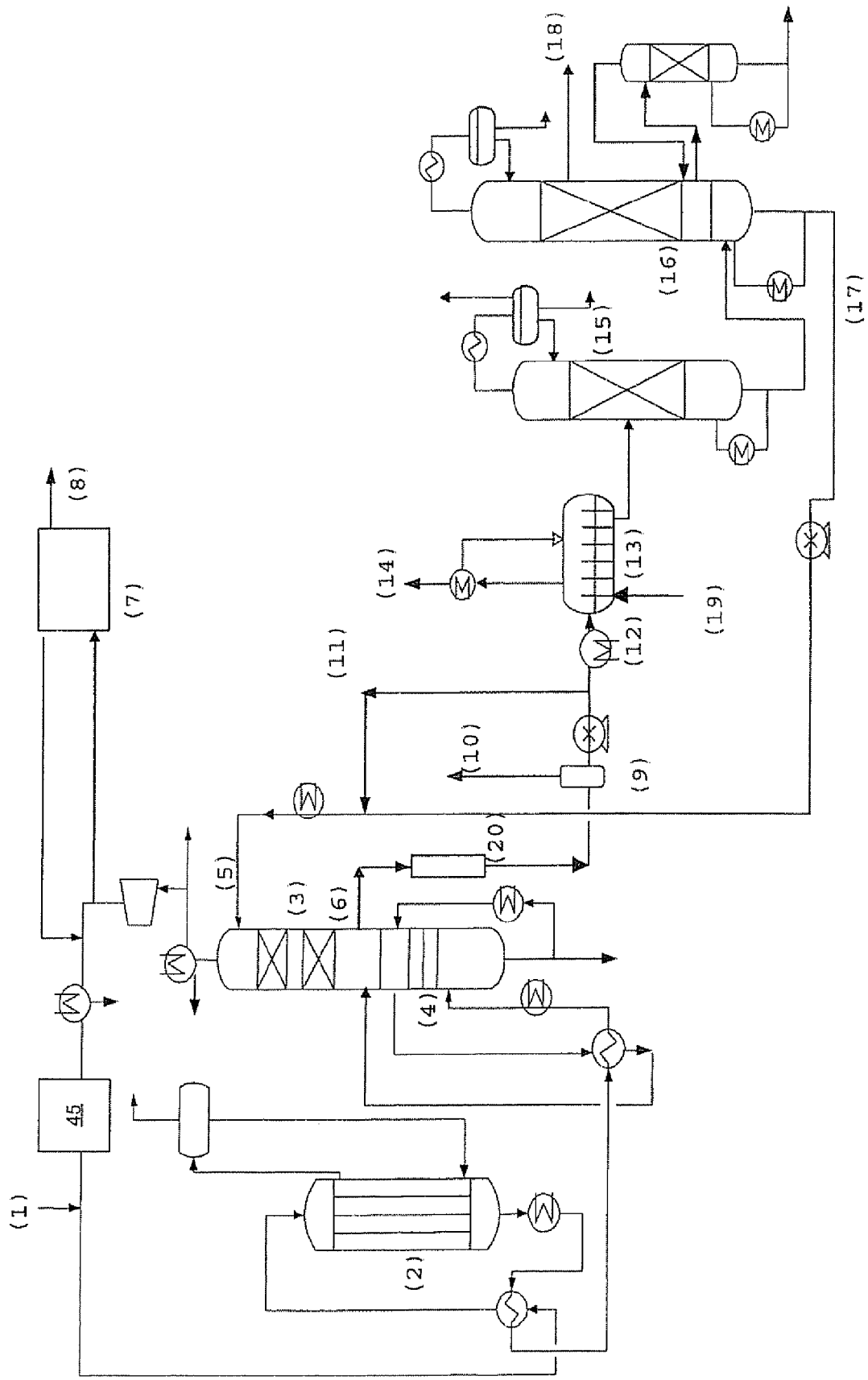
FIG. 2 is a schematic diagram showing a process according to another embodiment of the invention.

FIG. 2:

FIG. 2 shows an alternative preferred embodiment of the process of the invention wherein homogeneous carboxylation and hydrolysis catalysts are both present in the lean absorbent (5) that is supplied to the ethylene oxide absorber (3). The fat absorbent stream from the ethylene oxide absorber (3) is supplied to a finishing reactor (20) and then to a flash vessel (9). After the flash vessel the stream is split and one portion is fed to a heat exchanger (12) and is subsequently supplied to a hydrolysis reactor (13). The homogeneous catalysts are not separated in the flash vessel and remain in the fat absorbent that is supplied to the hydrolysis reactor. A solution comprising the carboxylation and hydrolysis catalysts dissolved in glycols (17) is withdrawn from the bottom of the MEG purification column (16) and is recycled to the ethylene oxide absorber (3) as lean absorbent (5) after mixing with the absorbent flow that is not supplied to the finishing reactor (11). In FIG. 2, the purification zone (45) is located in the recycle gas loop downstream from the carbon dioxide recovery section (7) and upstream from the addition of ethylene, oxygen, methane and reaction modifier.

Figure 3:
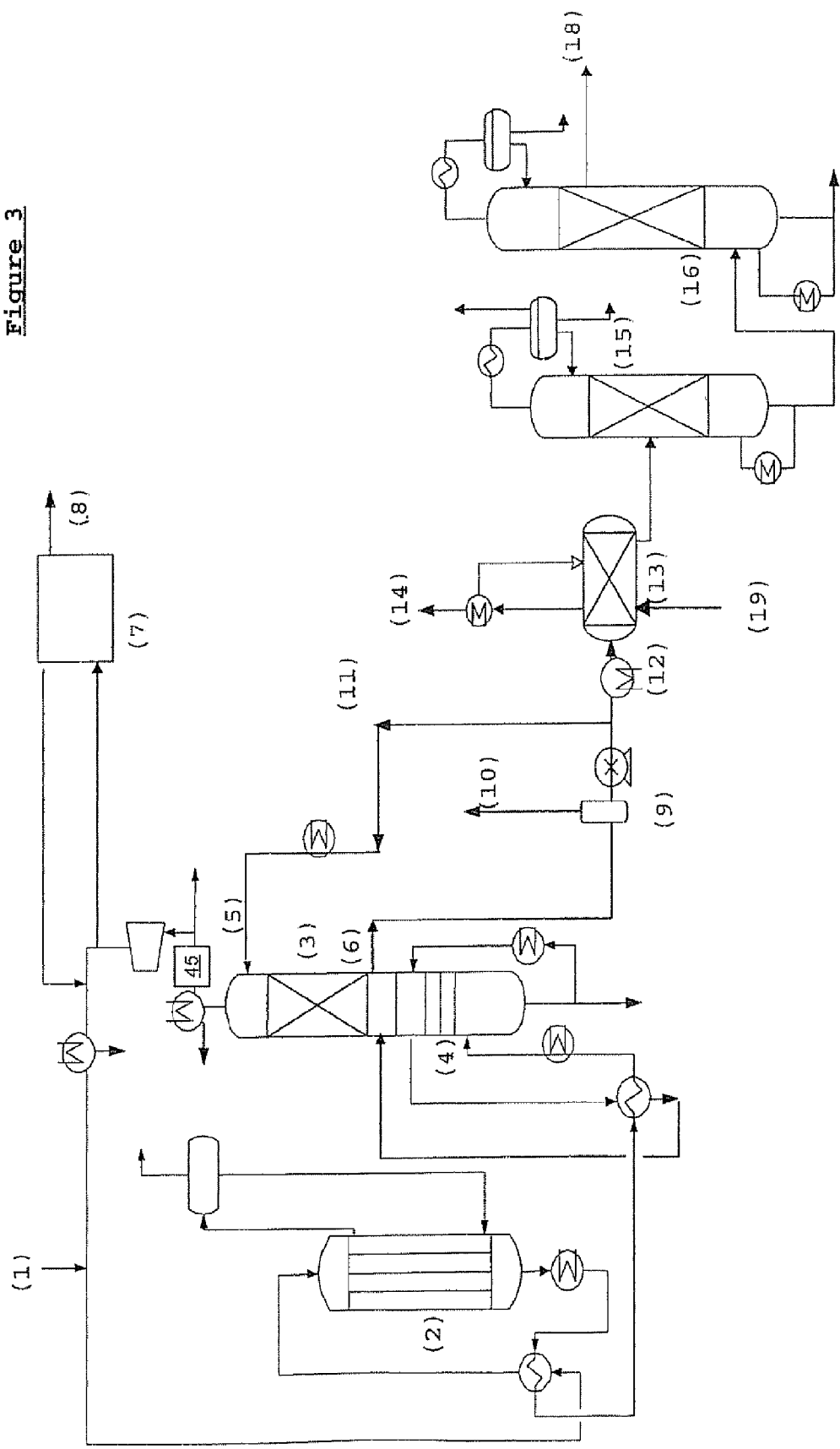
FIG. 3 is a schematic diagram showing a process according to another embodiment of the invention.

FIG. 3:

FIG. 3 shows yet another preferred embodiment of the process comprising a heterogeneous catalyst packing in the ethylene oxide absorber column (3) as well as a heterogeneous catalyst bed in the hydrolysis reactor (13). In this embodiment there is no requirement for catalyst separation or recirculation. No finishing reactor is used in this embodiment. In FIG. 3, the purification zone (45) is located in the recycle gas loop between the ethylene oxide absorber column (3) and the carbon dioxide recovery section (7).

Figure 4:
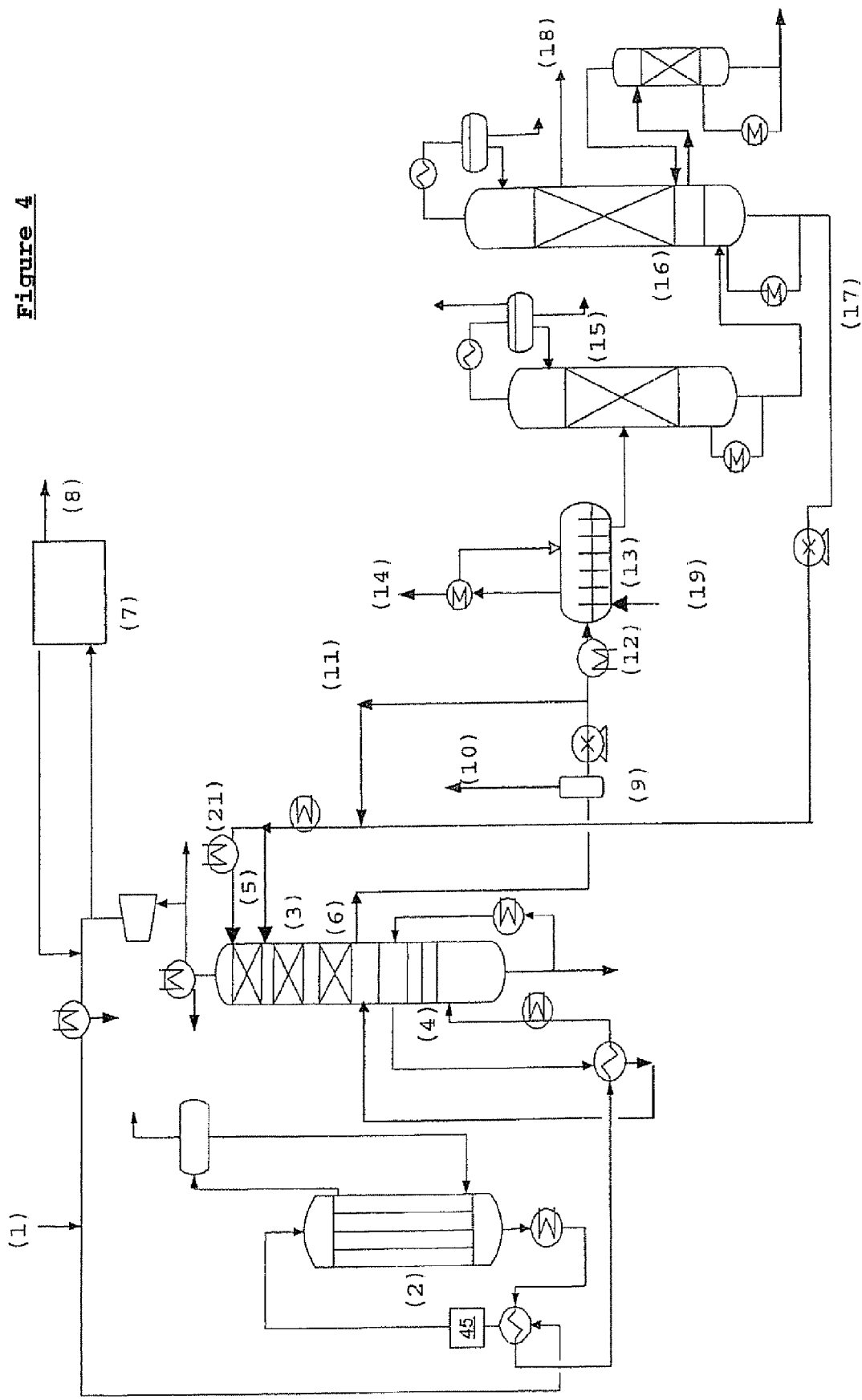
FIG. 4 is a schematic diagram showing a process according to another embodiment of the invention.

FIG. 4:

FIG. 4 shows an embodiment using homogeneous catalysts, where a portion of the lean absorbent is cooled in a heat exchanger (21) and is supplied to the ethylene oxide absorber column (3) above the top packing or top trays to absorb remaining ethylene oxide and/or contaminants in the top of the ethylene oxide absorber (3). No finishing reactor is used in this embodiment. In FIG. 4, the purification zone (45) is located in the recycle gas loop between the product/feed heat exchanger and the inlet of the ethylene epoxidation reactor (2).

Figure 5:
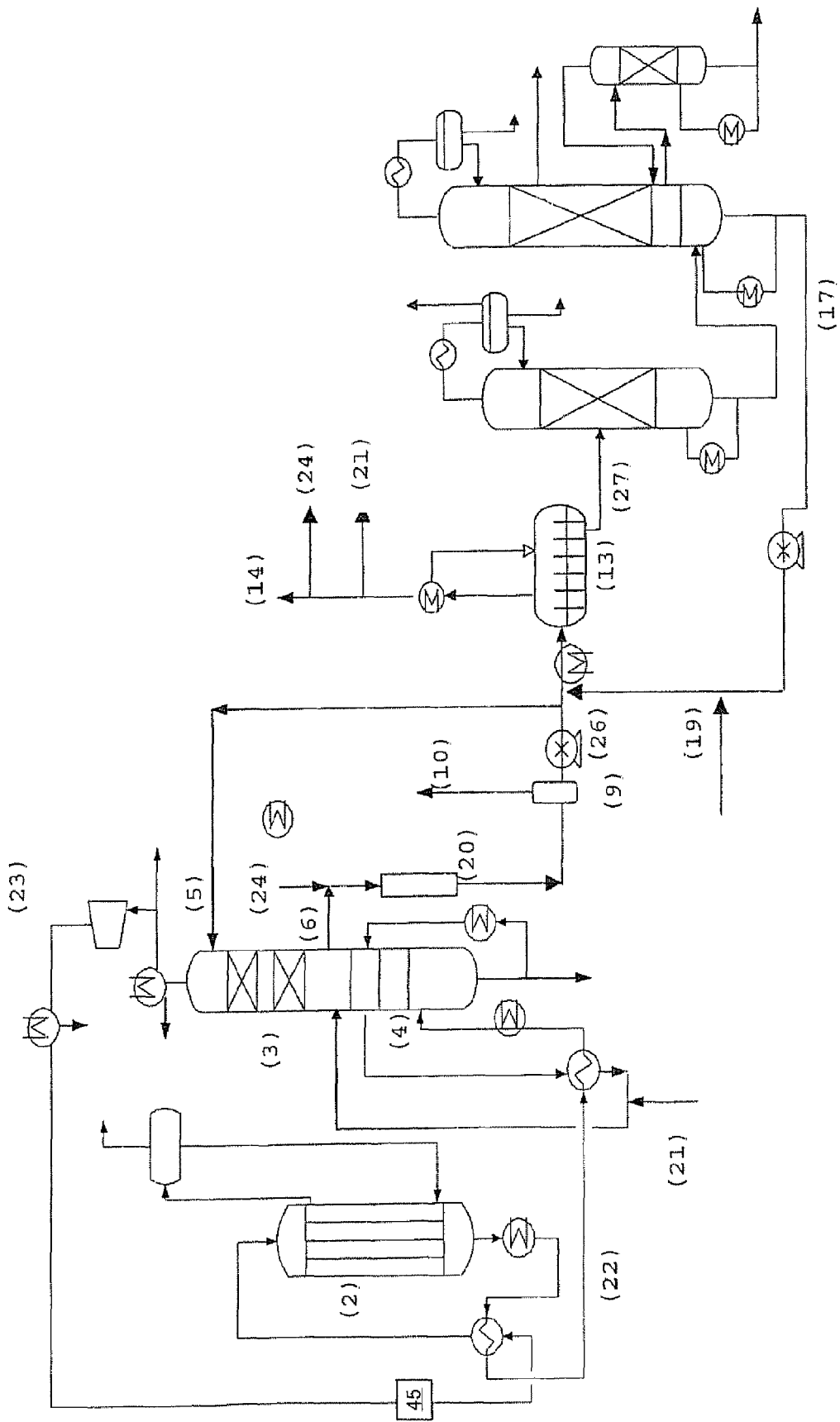
FIG. 5 is a schematic diagram showing a process according to another embodiment of the invention.

FIG. 5:

FIG. 5 shows an embodiment of the process using a heterogeneous catalyst packing in the ethylene oxide absorber column (3) and a homogeneous catalyst in the hydrolysis reactor (13). In this embodiment, the carbon dioxide content of the gases (23) leaving the ethylene oxide absorber (3) is sufficiently low that there is no requirement to recover carbon dioxide from this gas stream. In FIG. 5, the purification zone (45) is located in the recycle gas loop downstream from the addition of ethylene, oxygen, methane and reaction modifier and upstream from the product/feed heat exchanger.

Figure 6:
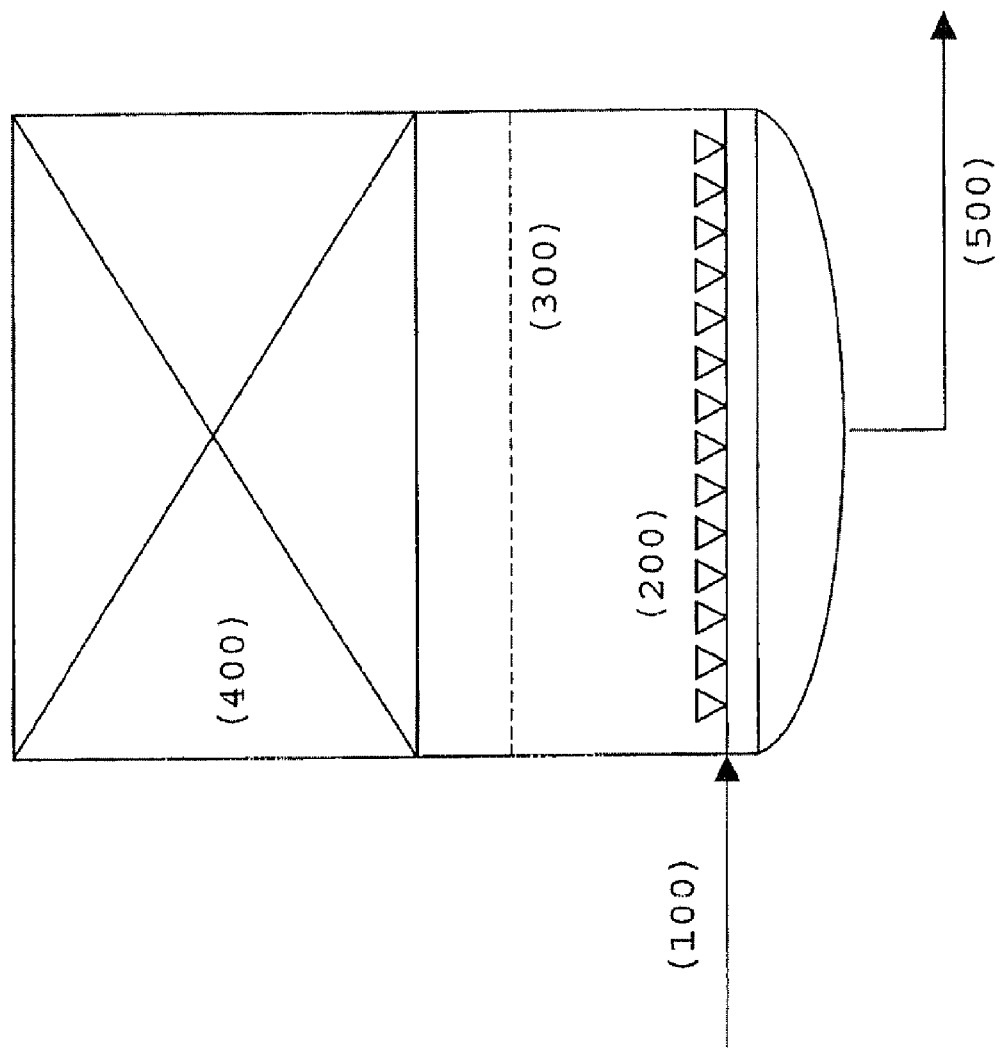
FIG. 6 is a schematic diagram showing an embodiment of the bottom of the alkylene oxide absorber column.

FIG. 6:

FIG. 6 describes an embodiment of the bottom of the ethylene oxide absorber column, where carbon dioxide gas (100) is supplied to the liquid though nozzles (200). The liquid level (300) is maintained well below the bottom tray or below the bottom of the column packing (400). Fat absorbent (500) leaves at the bottom.

Figure 7:
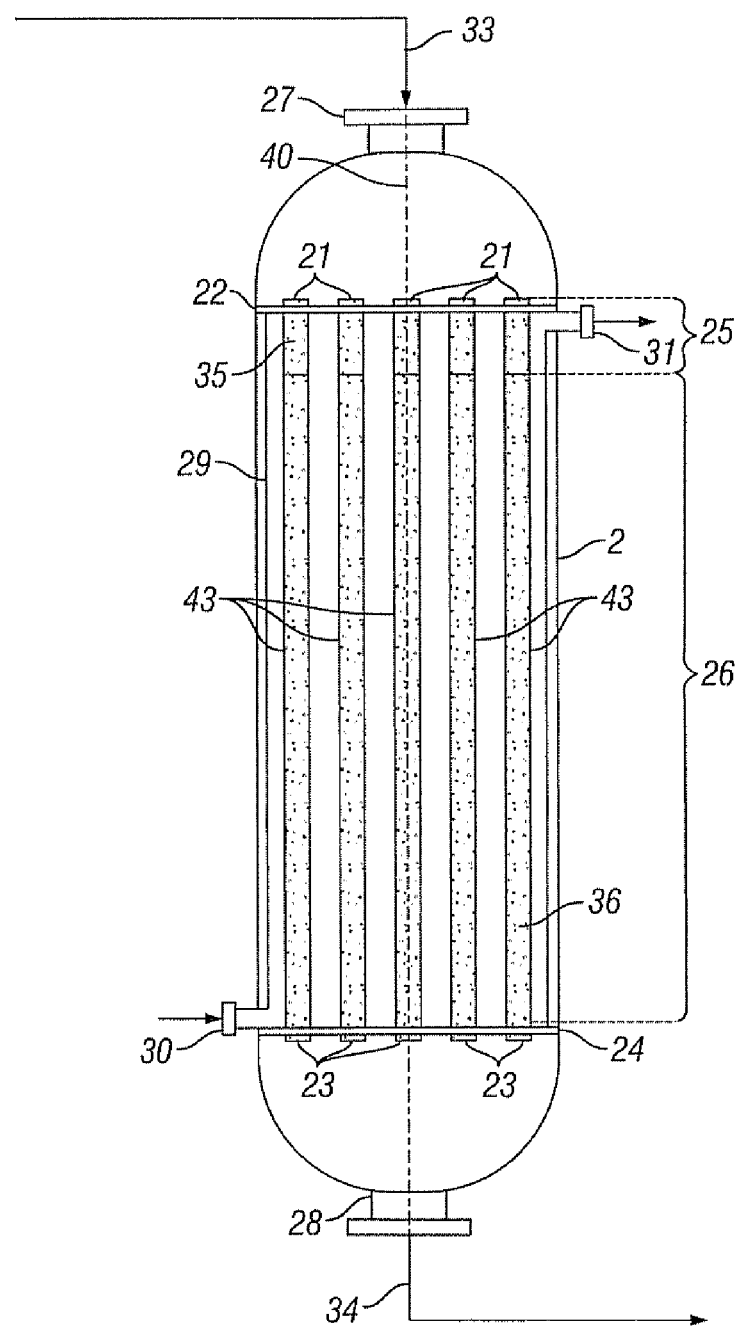
FIG. 7 is a schematic diagram showing an embodiment where the purification zone is located in the epoxidation reactor vessel within the epoxidation reactor tubes upstream from the epoxidation zone.

FIG. 7:

FIG. 7 describes an embodiment where the purification zone is located within the epoxidation reactor tubes. The epoxidation reactor (2) comprises a shell-and-tube heat exchanger reactor vessel having a substantially vertical vessel and a plurality of open-ended reactor tubes (43) positioned substantially parallel to the central longitudinal axis (40) of the epoxidation reactor vessel (2). The upper ends (21) of the reactor tubes (43) are connected to a substantially horizontal upper tube plate (22) and the lower ends (23) of the reactor tubes (43) are connected to a substantially horizontal lower tube plate (24). The upper tube plate (22) and the lower tube plate (24) are supported by the inner wall of the reactor vessel (2). The plurality of reactor tubes (43) contain a purification zone (25) and an epoxidation zone (26) positioned downstream from the purification zone (25). The purification zone (25) contains a purification absorbent (35). The epoxidation zone (26) contains an epoxidation catalyst (36). The epoxidation zone (26) is supported in the reactor tubes (43) by a catalyst support means (not shown) arranged in the lower ends (23) of the reactor tubes (43). Components of the feed (33), such as the alkene, oxygen and recycle gas, enter the reactor vessel (2) via one or more inlets such as inlet (27) which are in fluid communication with the upper ends (21) of the reactor tubes (43). The epoxidation reaction product (34) exits the epoxidation reactor vessel (2) via one or more outlets such as outlet (28) which are in fluid communication with the lower ends (23) of the reactor tubes (43). The heat exchange fluid enters the heat exchange chamber (29) via one or more inlets such as inlet (30) and exits via one or more outlets such as outlet (31). The heat exchange chamber (29) may be provided with baffles (not shown) to guide the heat exchange fluid through the heat exchange chamber (29).

Figure 8:
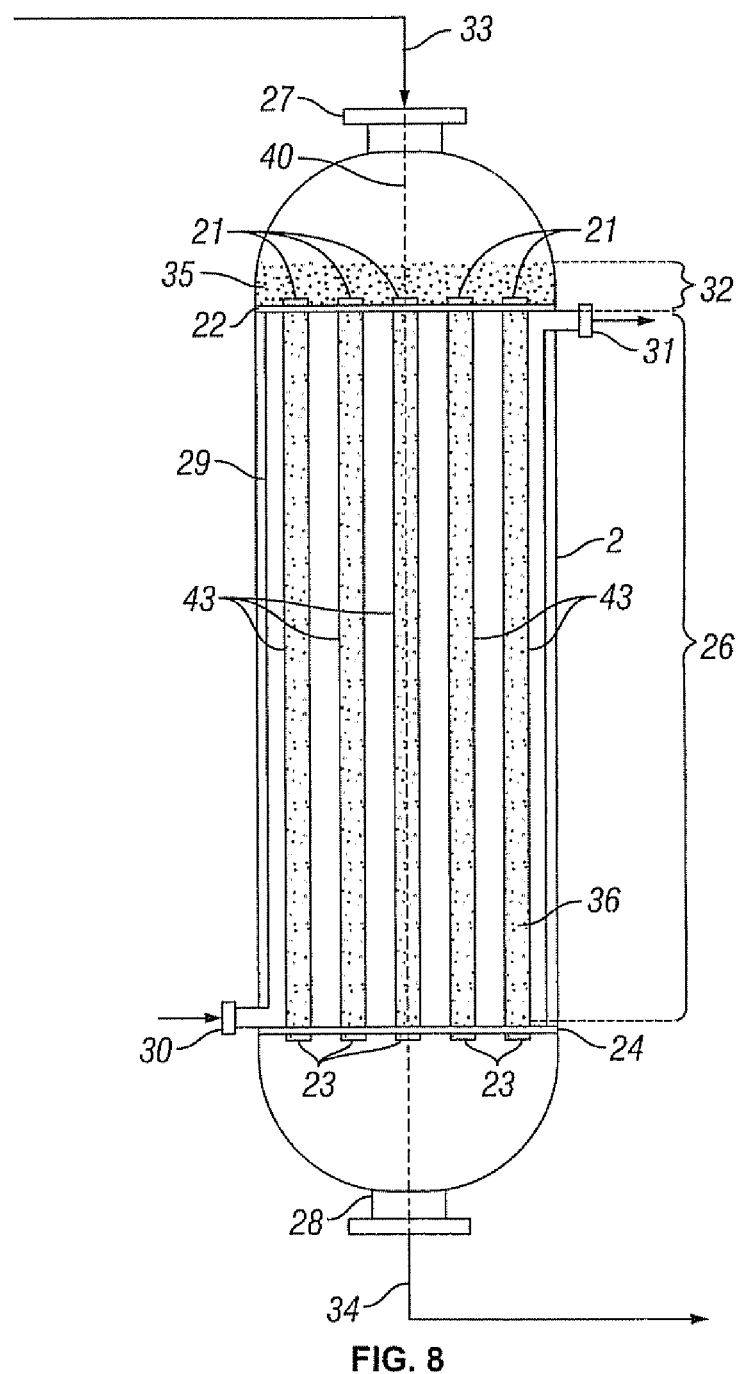
FIG. 8 is a schematic diagram showing an embodiment where the purification zone is located in the epoxidation reactor vessel upstream from the reactor tubes and the epoxidation zone.

FIG. 8:

FIG. 8 is a schematic view of an epoxidation reactor (2) similar to FIG. 7 except that the purification zone (32) is positioned upstream from the reactor tubes (43).

Example 1

Guard beds were used in these experiments to block gas-phase organic bromides. Several materials were used but the one which performed the best was a material comprised of silver and potassium supported on alumina. The guard beds were placed in a nitrogen stream that contained 1100 ppmv methyl bromide (pressure=1 atm, T=170° C., GHSV=3200 hr$^{-1}$). This environment is a more difficult environment for the blocking of organic bromides than the environment in the process of the present invention because no oxidizing agent is present in this experiment. The presence of an oxidizing agent should enhance the rate at which bromine-containing compounds react with the active surface of the guard bed material.

The experiments were carried out in a microreactor to which was delivered controlled flowrates of "stock methyl bromide" diluted with pure $N_2$ to achieve the desired MeBr concentration (1% v MeBr, balance $N_2$). The outlet line led to an auxiliary gas chromatograph that was configured to measure very low levels of organic halides (sampling τ=30 min) A description of the GC configuration is provided in Table 1. The instrument was first calibrated for measuring methyl bromide delivered over the range 0-1200 ppmv, with primary emphasis placed on accurate measurement in the sub-ppm range. Once experiments began, methyl bromide levels in the outlet stream were recorded twice per hour.

The following guard bed materials were evaluated:

A. "Ag/K/$Al_2O_3$"—this material was prepared by aqueous silver nitrate plus potassium nitrate vacuum impregnation onto 1.3 mm trilobe Criterion alumina extrudates (S.A=100-150 m$^2$/g), followed by centrifugation for 2 minutes at 200 rpm and drying in a shaking basket for 10 minutes at 170° C. The dried material was then calcined in air for 15 minutes at 250° C. Elemental analysis indicates that the final material contained 23.4% w Ag and 2.72% w K.

B. "Cu/$Al_2O_3$"—KL-5715 catalyst made by KataLeuna which consists of 10% w CuO on alumina.

C. "Cu/Zn/$Al_2O_3$"—KL-4211 catalyst made by KataLeuna which has a bulk composition of 48% w CuO/36% w ZnO/16% w $Al_2O_3$.

In Experiment 1, guard bed material Ag/K/$Al_2O_3$ was crushed and sieved to 30-40 mesh size. 1.00 g material was loaded into a U-shaped stainless steel microreactor tube (0.25" OD, 0.18" ID) and the crushed material was secured in place with small glass wool plugs. The tube was placed in the liquid metal temperature control bath and affixed to the feed delivery and exit systems. As feedstock flow was initiated, data collection via the auxiliary GC commenced. Data collection continued until at least 50% breakthrough was observed, which is to say, until the concentration of methyl bromide in the outlet stream reached at least 50% of the level being fed. The net amount of bromine sorbed per time interval was calculated by multiplying the amount of bromine fed per period times the fraction of methyl bromide that was not observed in the outlet stream.

Experiments 2-5 were conducted in like manner. In Experiment 2, the concentration and space velocity of the bromide stream was varied several times during the run. In Experiments 3-5, MeBr concentration and space velocity remained constant throughout. Complete descriptions of the experimental conditions are given in Table 1.

The experimental results are summarized in Table 1. Guard bed sorption effectiveness was rated by comparing cumulative sorption at the point where "% breakthrough" had reached 20% (BT-20%). At BT-20%, the GC detects a concentration of methyl bromide exiting the guard bed that is equal to 20% of the inlet concentration—Elemental Bromine Absorbed (as % w of Guard Bed Mass). For example, a value of 20% means that each gram of guard bed material has sorbed 0.2 g bromine.

The very high bromide concentration combined with high space velocity used in Experiment 1 immediately overwhelmed the bed, resulting in essentially full breakthrough even in the first sampling interval.

For Experiment 2, both the concentration and the space velocity were reduced. With a few mid-course modifications, "100% breakthrough" was achieved in about a week. At the point of BT-20%, it was calculated (basis summation of point-by-point sorption) that the bed had sorbed an amount of methyl bromide equivalent to 14.3% w of its mass.

Experiment 3 utilized the highest flowrate (325 cc/min=GHSV 3200 hr$^{-1}$) and the highest bromide concentration (1100 ppmv) from Experiment 2 but was conducted at a much lower temperature (170° C. vs. 250° C. in Experiment 2). Counterintuitively (for a presumably chemisorption phenomenon), the lower temperature was significantly more effective for bromine capture when using the Ag/K/$Al_2O_3$ guard bed material which sorbed 24.8% of its weight in bromine by the time BT-20% was reached.

To confirm the impressive results of this experiment, the spent bed material was submitted for bromine analysis by x-ray fluorescence. The spent bromine-loaded material contained 21.9% w bromine, which corresponds to 28.0% w bromine basis the original 5.0 g mass of the guard bed. By the time methyl bromide flow ceased in Experiment 3, it was calculated (by summing all of the bromine absorbed for each sampling interval) that the bed had sorbed 25.6% w bromine basis the original 5.0 g mass of the guard bed. Given the challenge of metering low levels of methyl bromide to the bed and accurately measuring even lower levels exiting the bed, the calculated 25.6% w value is considered to be in very good agreement with the analytical 28.0% w value.

Experiments 4 and 5 measured the methyl bromide sorption capacity of the selected copper-based and copper-zinc-based materials, using the same conditions as Experiment 3. Neither of the copper-containing materials was as effective as silver on alumina but the copper/alumina material performed reasonably well.

TABLE 1

Interception of Methyl Bromide from MeBr/N$_2$ Stream
Agilent 6890 Gas Chromatograph fitted with heated valve box (80° C.) containing 3
Valco valves for stream selection, sample stream isolation and sample injection.
Agilent GasPro 60 m × 0.32 mm part# 113-4362 column with helium carrier
flow of 3.5 ml/min (velocity 44 cm/sec) in the constant flow mode.
Inlet temperature 250° C.; Purge flow = 3.5 ml/min; Oven temperature 250° C.; FID detector.

| Experiment | Guard Bed | GB Mass (g) | Bed Temp (° C.) | Flow rate (cc/min) | GHSV (hr$^{-1}$) | [MeBr] (ppmv) | BT-20% (g Br per g GB) |
|---|---|---|---|---|---|---|---|
| #1 | Ag/K/Al$_2$O$_3$ | 1.0 | 250 | 325 | 16,000 | 10,000 | ~0 |
| #2 | Ag/K/Al$_2$O$_3$ | 5.0 | 250 | 100/325/100 | 980/3200/980 | 120/120/1100 | 14.3 |
| #3 | Ag/K/Al$_2$O$_3$ | 5.0 | 170 | 325 | 3200 | 1100 | 24.8 |
| #4 | Cu/Al$_2$O$_3$ | 5.0 | 170 | 325 | 3200 | 1100 | 6.5 |
| #5 | Cu/Zn/Al$_2$O$_3$ | 5.0 | 170 | 325 | 3200 | 1090 | 0.3 |

What is claimed is:

1. A reaction system for the production of an alkylene carbonate and/or alkylene glycol comprising:
an epoxidation zone containing an epoxidation catalyst located within an epoxidation reactor;
a carboxylation zone containing an bromide-containing carboxylation catalyst located within an alkylene oxide absorber; and
a purification zone containing a purification absorbent capable of reducing the quantity of bromide-containing impurities in a feed comprising a recycle gas, which purification zone is located upstream from the epoxidation zone.

2. The reaction system of claim 1 wherein the epoxidation reactor is a shell-and-tube heat exchanger comprising a plurality of reactor tubes positioned substantially parallel to the central longitudinal axis of the epoxidation reactor; wherein the upper ends of the reactor tubes are connected to a substantially horizontal upper tube plate and the lower ends of the reactor tubes are connected to a substantially horizontal lower tube plate; and wherein the epoxidation catalyst is in the form of a packed bed positioned within the reactor tubes.

3. The reaction system of claim 2 wherein the purification zone is located within the reactor tubes.

4. The reaction system of claim 2 wherein the purification zone is located within the epoxidation reactor upstream from the reactor tubes.

5. The reaction system of claim 1 wherein the purification zone comprises a separate purification vessel located upstream from the epoxidation zone which comprises a separate epoxidation reactor.

6. The reaction system of claim 1 wherein the purification absorbent comprises a metal having an atomic number of 22 through 44 or 82.

7. The reaction system of claim 1 wherein the purification absorbent comprises silver.

8. The reaction system of claim 1 wherein the purification absorbent comprises silver, an alkali or alkaline earth metal component, and a support material having a surface area of more than 20 m$^2$/g.

9. The reaction system of claim 1 wherein the purification absorbent is a spent epoxidation catalyst which has produced more olefin oxide than the epoxidation catalyst.

10. The reaction system of claim 1 wherein the purification absorbent comprises a basic zeolite.

* * * * *